(12) United States Patent
Takakura et al.

(10) Patent No.: US 10,266,857 B2
(45) Date of Patent: Apr. 23, 2019

(54) METHOD FOR PRODUCING Nε-ACYL-L-LYSINE

(71) Applicant: AJINOMOTO CO., INC., Tokyo (JP)

(72) Inventors: Jun Takakura, Kanagawa (JP);
Hiroyuki Nozaki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/955,267

(22) Filed: Apr. 17, 2018

(65) Prior Publication Data

US 2018/0230502 A1    Aug. 16, 2018

Related U.S. Application Data

(63) Continuation of application No. PCT/JP2016/083457, filed on Nov. 11, 2016.

(30) Foreign Application Priority Data

Nov. 12, 2015   (JP) ................. 2015-222466

(51) Int. Cl.
*C12P 13/04*    (2006.01)
*C12P 13/08*    (2006.01)
*C12N 9/80*    (2006.01)

(52) U.S. Cl.
CPC ............... *C12P 13/08* (2013.01); *C12N 9/80* (2013.01); *C12Y 305/01014* (2013.01)

(58) Field of Classification Search
CPC .... C12P 13/08; C12Y 305/01017; C12N 9/80
See application file for complete search history.

(56) References Cited

U.S. PATENT DOCUMENTS

| | | |
|---|---|---|
| 7,745,182 B2 | 6/2010 | Nozaki et al. |
| 7,888,079 B2 | 2/2011 | Nakanishi et al. |
| 2003/0157670 A1 | 8/2003 | Nakanishi et al. |
| 2004/0106172 A1 | 6/2004 | Nakanishi et al. |
| 2007/0298469 A1 | 12/2007 | Nakanishi et al. |

FOREIGN PATENT DOCUMENTS

| | | |
|---|---|---|
| JP | 2003-210164 A | 7/2003 |
| JP | 2004-081107 A | 3/2004 |
| WO | WO2006/088199 A1 | 8/2006 |
| WO | WO2010/067871 A1 | 6/2010 |

OTHER PUBLICATIONS

Machine translation of WO 2010/067871 A1, 17 pages, retrieved from Google Patents on Aug. 10, 2018 (Year: 2018).*
Bers et al., "HylA, an Alternative Hydrolase for Initiation of Catabolism of the Phenylurea Herbicide Linuron in *Variovorax* sp. Strains ", Appl. Environ. Microbiol. 79:5258-5263, 2013 (Year: 2013).*
International Search Report and Written Opinion for PCT Patent App. No. PCT/JP2016/083457 (dated Jan. 31, 2017) with English translation.
Accession No. ACY49244, Definition: Amidohydrolase 3 [Rhodothermus marinus DSM 4252], [online], publication date: Dec. 11, 2013, [retrieval date: Jan. 17, 2017], Database UniProt/GenSeq, Internet: <URL: https://www.ncbi.nlm.nih.gov/protein/acy49244>.
Koreishi, M., et al., "Efficient Nε-lauroyl-L-lysine production by recombinant ε-lysine acylase from Streptomyces mobaraensis," J. Biotechnol. 2009;141:160-165.
Chibata, I., et al., "Studies on Amino Acids. XIII. A Survey of the ε-Lysine Acylase Activity in Microorganisms," Bull. Agr. Chem. Soc. Japan 1960;24(1):31-36.
International Search Report and Written Opinion for PCT Patent App. No. PCT/JP2016/083457 (dated Feb. 16, 2016) with English translation.
International Preliminary Report on Patentability for PCT Patent App. No. PCT/JP2016/083457 (dated Jun. 27, 2017).

* cited by examiner

*Primary Examiner* — David Steadman
(74) *Attorney, Agent, or Firm* — Cermak Nakajima & McGowan LLP; Shelly Guest Cermak

(57) ABSTRACT

The present invention provides a method for producing Nε-dodecanoyl-L-lysine using an enzyme having properties suitable for the industrial production of Nε-dodecanoyl-L-lysine. More specifically, the present invention provides a method for producing Nε-acyl-L-lysine including reacting a carboxylic acid or a salt thereof and L-lysine or a salt thereof in the presence of a protein having an amino acid sequence of SEQ ID NO: 1; a protein having an amino acid sequence in which one or several amino acid residues are inserted, added, deleted, or substituted in the amino acid sequence of SEQ ID NO: 1 and having Nε-acyl-L-lysine-specific aminoacylase activity; and a protein which has 90% or higher homology with the amino acid sequence of SEQ ID NO: 1 and having Nε-acyl-L-lysine-specific aminoacylase activity.

15 Claims, 7 Drawing Sheets
Specification includes a Sequence Listing.

● ELA derived from *Rhodothermus marinus*
(an enzyme used in the present invention)

○ ELA derived from *Streptomyces mobarensis*
(an enzyme disclosed in WO2006/088199)

● ELA derived from *Rhodothermus marinus*
(an enzyme used in the present invention)

○ ELA derived from *Streptomyces mobarensis*
(an enzyme disclosed in WO2006/088199)

● ELA derived from *Rhodothermus marinus* (an enzyme used in the present invention)

○ ELA derived from *Streptomyces mobarensis* (an enzyme disclosed in WO2006/088199)

● ELA derived from *Rhodothermus marinus* (an enzyme used in the present invention)

○ ELA derived from *Streptomyces mobarensis* (an enzyme disclosed in WO2006/088199)

FIG. 5

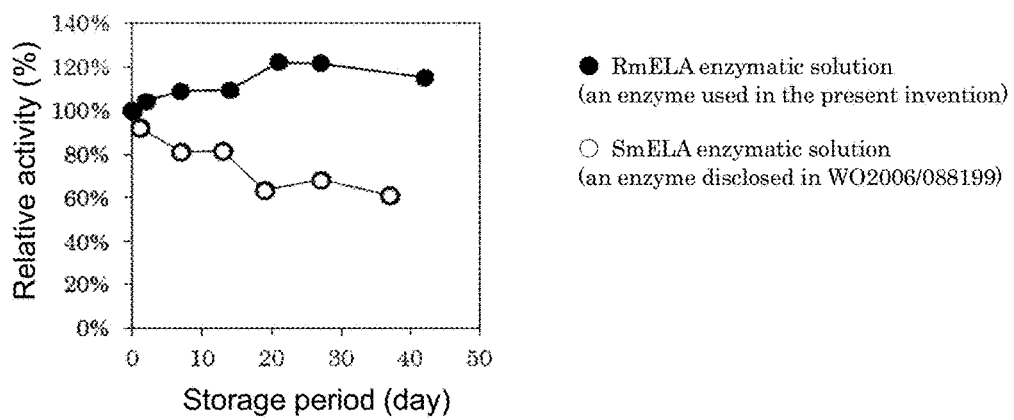

(a) Storage at 4°C

● RmELA enzymatic solution
(an enzyme used in the present invention)

○ SmELA enzymatic solution
(an enzyme disclosed in WO2006/088199)

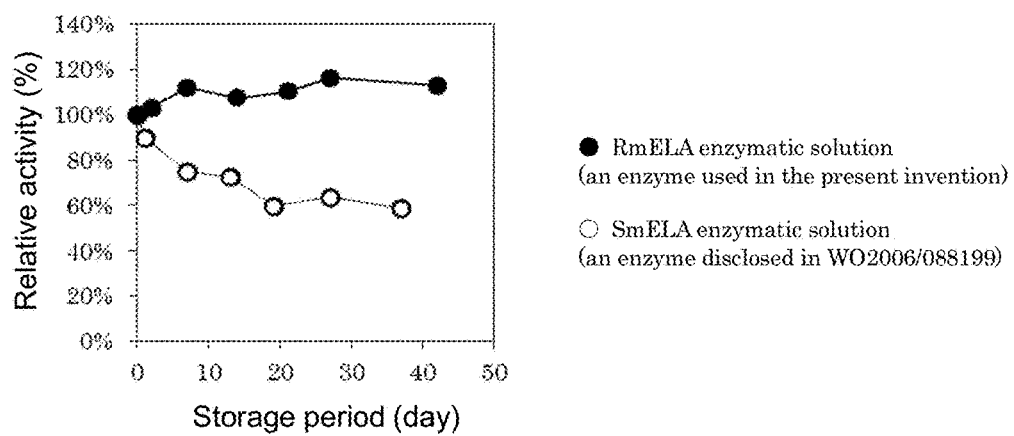

(b) Storage at 15°C

● RmELA enzymatic solution
(an enzyme used in the present invention)

○ SmELA enzymatic solution
(an enzyme disclosed in WO2006/088199)

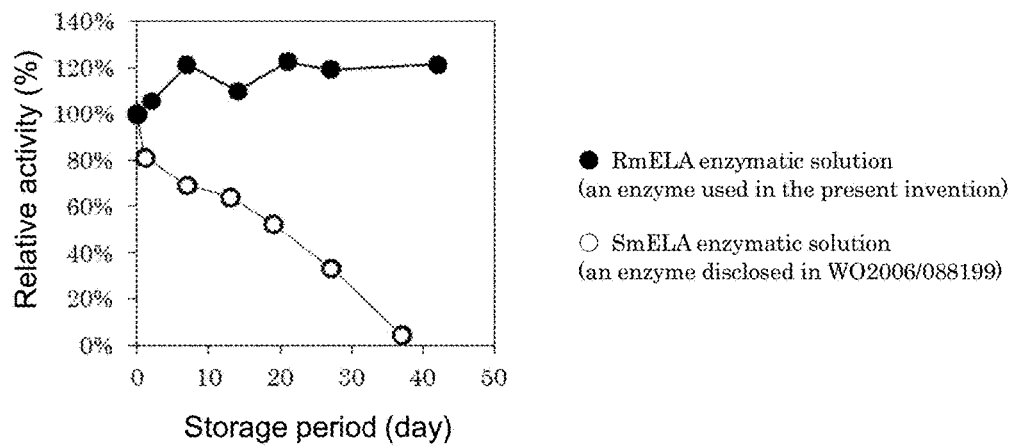

(c) Storage at 25°C

● RmELA enzymatic solution
(an enzyme used in the present invention)

○ SmELA enzymatic solution
(an enzyme disclosed in WO2006/088199)

METHOD FOR PRODUCING Nε-ACYL-L-LYSINE

This application is a Continuation of, and claims priority under 35 U.S.C. § 120 to International Application PCT/JP2016/083457, filed Nov. 11, 2016, and claims priority therethrough under 35 U.S.C. § 119 to Japanese Patent Application No. 2015-222466, filed Nov. 12, 2015, the entireties of which are both incorporated by reference herein. Also, the Sequence Listing filed electronically herewith is hereby incorporated by reference (File name: 2018-04-17T_US-575_Seq_List; File size: 12 KB; Date recorded: Apr. 17, 2018).

FIELD OF THE INVENTION

The present invention relates to a method for producing Nε-acyl-L-lysine.

BRIEF DESCRIPTION OF THE RELATED ART

The versatile compound Nε-acyl-L-lysine is useful as an amphoteric surfactant raw material because of its structural characteristics and low environmental loads. Nε-acyl-L-lysine is useful as an ingredient in general detergents, disinfecting agents, fiber softeners, anticorrosives, flotation agents, adhesives, clarifying agents, dye fixing agents, antistatic agents, emulsifiers, surfactants for cosmetics and the like. In particular, a feature of Nε-acyl-L-lysine is that it is extremely difficult to dissolve in water and normal organic solvents, and hence is useful as a water repellant, antioxidant, lubricant, and the like, and is thus receiving attention in the field of cosmetics, lubricants, and the like as a new organic powder material.

Non-enzymatic chemical methods have been conventionally used to produce Nε-acyl-L-lysine; however, these methods are complicated and require the use of the heavy metal copper. Therefore, production methods for Nε-acyl-L-lysine using milder conditions, such as via the use of an enzyme, are desirable.

A few enzymes have been reported to be able to specifically hydrolyze Nε-acyl-L-lysine, including enzymes native to *Achromobacter pestifer*, rat kidney, *Pseudomonas* sp. KT-83, and the like. Synthesis of Nε-acyl-L-lysine using any of these enzymes has not been previously reported.

Japanese Patent Application Laid-open No. 2003-210164 discloses that an enzyme for hydrolyzing and synthesizing capsaicin can be used in the synthesis of Nε-acyl-L-lysine. Similarly, Japanese Patent Application Laid-open No. 2004-81107 discloses that an enzyme for hydrolyzing and synthesizing capsaicin, as described in Japanese Patent Application Laid-open No. 2003-210164, is able to produce Nε-dodecanoyl (lauroyl)-L-lysine with a yield of 95%. However, Japanese Patent Application Laid-open No. 2004-81107 also discloses that the reaction by this enzyme requires a long reaction time, as long as two days, and that this enzyme is highly reactive not only for an ε-amino group, but also for an α-amino group, and thus produces a mixture of Nα-dodecanoyl-L-lysine and Nε-dodecanoyl-L-lysine in the end.

WO 2006/088199 and WO 2010/067871 disclose that *Streptomyces mobarensis* produces an enzyme that is capable of acylating the ε-amino group of L-lysine, and that Nε-dodecanoyl-L-lysine can be specifically synthesized from L-lysine hydrochloride and dodecanoic acid by this enzyme purified from *Streptomyces mobarensis*.

SUMMARY OF INVENTION

Conventional enzymes are not satisfactory for the industrial production of Nε-dodecanoyl-L-lysine in their performance. For example, conventional enzymes cannot necessarily specifically acylate the ε-amino group of L-lysine. Therefore, they produce a mixture of Nα-dodecanoyl-L-lysine and Nε-dodecanoyl-L-lysine as described above, and hence have the drawback of requiring a complicated process to separate the compounds from each other. In addition, conventional enzymes lack stability and are easily inactivated, and thus are difficult for use in industrial production.

An enzyme is described herein that overcomes all of these drawbacks, for example, the enzyme described herein is stable and is capable of specifically acylating the ε-amino group of L-lysine, and hence can specifically produce Nε-acyl-L-lysine.

It is an aspect of the present invention to provide a method for producing Nε-acyl-L-lysine comprising reacting a carboxylic acid or a salt thereof and L-lysine or a salt thereof in the presence of a protein selected from the group consisting of: (A) a protein comprising the amino acid sequence of SEQ ID NO: 1; (B) a protein comprising the amino acid sequence of SEQ ID NO: 1, but wherein one or several amino acid residues are inserted, added, deleted, or substituted, and wherein said protein has Nε-acyl-L-lysine-specific aminoacylase activity; (C) a protein comprising an amino acid sequence having 70% or higher homology with the amino acid sequence of SEQ ID NO: 1, and wherein said protein has Nε-acyl-L-lysine-specific aminoacylase activity.

It is a further aspect of the present invention to provide the method as described above, wherein the protein is native to a bacterium belonging to the genus *Rhodothermus*.

It is a further aspect of the present invention to provide the method as described above, wherein the protein is a purified enzyme.

It is a further aspect of the present invention to provide the method as described above, wherein said reacting is carried out using: a) a microorganism producing the protein, or b) a treatment solution comprising a microorganism producing the protein.

It is a further aspect of the present invention to provide the method as described above, wherein the microorganism is a bacterium belonging to the genus *Corynebacterium*.

It is a further aspect of the present invention to provide the method as described above, wherein the microorganism is *Corynebacterium glutamicum*.

It is a further aspect of the present invention to provide the method as described above, wherein the carboxylic acid has five or more carbon atoms.

It is a further aspect of the present invention to provide the method as described above, wherein the carboxylic acid is selected from the group consisting of octanoic acid, dodecanoic acid, tetradecanoic acid, hexadecanoic acid, linoleic acid, oleic acid, benzoic acid, methoxymethyl benzoic acid, phenylpropionic acid, cinnamoyl acid, and methoxycinnamoyl acid.

It is a further aspect of the present invention to provide the method as describe aboved, wherein the carboxylic acid is octanoic acid or dodecanoic acid, and Nε-acyl-L-lysine is Nε-octanoyl-L-lysine or Nε-dodecanoyl-L-lysine.

It is a further aspect of the present invention to provide the method as described above, wherein said reacting is carried out in an aqueous solvent.

It is a further aspect of the present invention to provide the method as described above, wherein the treatment solution is a microbicidal treatment solution.

It is a further aspect of the present invention to provide the method as described above, wherein said reacting is carried out at 40° C. or higher.

It is a further aspect of the present invention to provide the method as described above, wherein said carboxylic acid or a salt thereof is non-emulsified.

It is a further aspect of the present invention to provide the method as described above, wherein the reaction is carried out in a solution comprising the carboxylic acid or a salt thereof, or L-lysine or a salt thereof, at a concentration of 500 mmol/L or higher.

The protein as described herein has excellent stability, particularly in solutions, and is temperature and pH stable. Consequently, the method carried out using such a protein is advantageous in that it is excellent in long-term reactivity and can be carried out in wide ranges of temperature and pH.

In addition, the protein used in the method as described herein has excellent resistance to heat treatment. Consequently, even after the microorganisms that produce the protein as described herein are killed by the heat treatment, the protein produced by the microorganisms is not inactivated, and therefore heat treatments can be favorably used for the reaction using this protein. This advantage is desirable also from the viewpoints of environmental safety and simplification of processes in that an enzymatic solution for use in the reaction can be easily prepared and sterilized.

The protein used in the method as described herein further maintains high activity under weak acid conditions. Consequently, the method as described herein carried out in the presence of such a protein is capable of improving the properties and characteristics of a crystal of Nε-acyl-L-lysine produced as described in detail herein.

In addition, the protein used in the method as described herein is resistant to inhibition by a substrates at a high concentration. The method as described herein carried out in the presence of such a protein can use a substrates at high concentrations, and thus has the advantage that a large amount of Nε-acyl-L-lysine can be produced.

BRIEF DESCRIPTION OF DRAWINGS

FIGS. 5a, b, and c are diagrams illustrating a storage stability comparison between ELA native to *Rhodothermus marinus*, as used in the method as described herein, and ELA (SmELA) enzymatic solution native to *Streptomyces mobarensis*, as disclosed in WO 2006/088199: (a) stored at 4° C.; (b) stored at 15° C.; and (c) stored at 25° C.

DETAILED DESCRIPTION OF EXEMPLARY EMBODIMENTS

Figure 1:
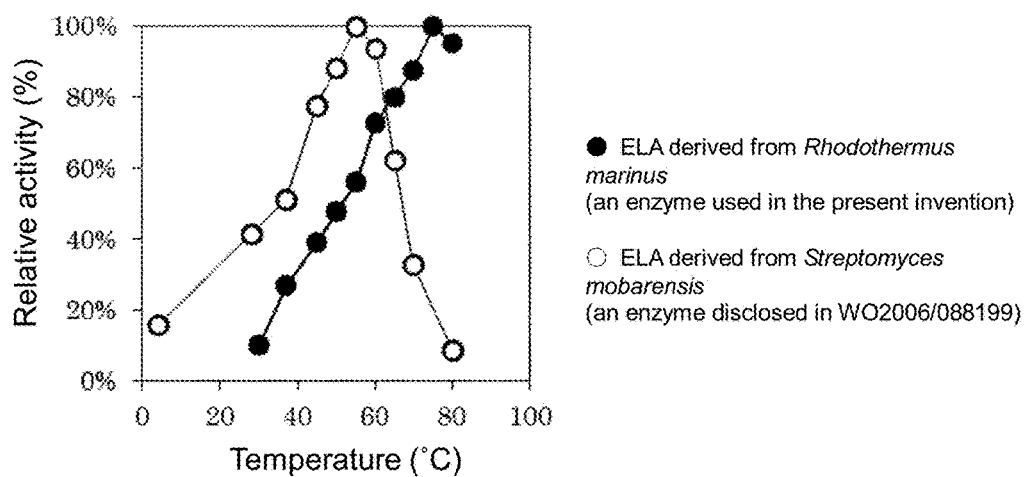
FIG. 1 is a diagram illustrating a temperature dependence comparison between ELA native to *Rhodothermus marinus*, as used in the method as described here, and ELA native to *Streptomyces mobarensis*, as disclosed in WO 2006/088199.

A method for producing Nε-acyl-L-lysine is described. The method as described herein includes the steps of reacting a carboxylic acid or a salt thereof and L-lysine or a salt thereof in the presence of a protein having the amino acid sequence of SEQ ID NO: 1; a protein having the amino acid sequence of SEQ ID NO: 1, but having one or several amino acid residues that are inserted, added, deleted, or substituted and that has Nε-acyl-L-lysine-specific aminoacylase activity; or a protein that is 90% or higher homologous with the amino acid sequence of SEQ ID NO: 1 and that has Nε-acyl-L-lysine-specific aminoacylase activity.

The protein having the amino acid sequence of SEQ ID NO: 1 has the following physicochemical properties:

(1) Action and substrate specificity: catalyzing the degradation and/or synthesis reaction of Nε-acyl-L-lysine;

(2) Optimum temperature range: about 75° C.;

(3) Optimum pH range: a pH of about 5;

(4) Temperature stability: not being inactivated by treatment at 80° C. for 60 minutes.

In the protein having an amino acid sequence of SEQ ID NO:1, one or several amino acid residues can be modified by one, two, three, or four kinds of mutations, such as deletion, substitution, addition, and/or insertion of one or more amino acid residues. The mutations of the amino acid residue(s) may be introduced into one region of an amino acid sequence or introduced to a plurality of different regions in the protein. The term "one or several" can indicate a number that does not greatly impair the activity of the protein. The number indicated by the term "one or several" can be, for example, 1 to 100, 1 to 80, 1 to 50, 1 to 30, 1 to 20, 1 to 10, or 1 to 5, such as one, two, three, four, or five.

The protein can be homologous to the amino acid sequence of SEQ ID NO: 1, and the homology percentage with the amino acid sequence of SEQ ID NO: 1 may be 70% or higher, 75% or higher, 80% or higher, 85% or higher, 90% or higher, 91% or higher, 92% or higher, 93% or higher, 94% or higher, 95% or higher, 96% or higher, 97% or higher, 98% or higher, or 99% or higher. The homology, that is, identity or similarity, of the amino acid sequence described above and a nucleotide sequence described below can be determined, for example, using the algorithm BLAST (Pro. Natl. Acad. Sci. USA, 90, 5873 (1993)) by Karlin and Altschul and FASTA (Methods Enzymol., 183, 63(1990)) by Pearson. Based on this algorithm BLAST, programs called BLASTP and BLASTN have been developed (see ncbi.nlm.nih.gov), and the homology can be calculated using the default settings of these programs. To calculate homology, a similarity value is calculated in terms of percentage with a setting of Unit Size to Compare=2 using the full-length polypeptide portion encoded in an ORF using GENETYX Ver. 7.0.9, software by Genetyx Corporation, adopting the Lipman-Pearson method, for example. Alternatively, identity may be calculated by using default parameter settings (Gap penalty=10, Extend penalty=0.5, and Matrix=EBLOSUM62) in the NEEDLE program (J. Mol. Biol. 1970; 48: 443-453) search. Among the values of the homology percentage derived by these calculations, the lowest value may be used.

The protein used in the method as described herein has Nε-acyl-L-lysine-specific aminoacylase activity, and thus is able to specifically produce Nε-acyl-L-lysine with excellent results. The term "Nε-acyl-L-lysine-specific aminoacylase activity" can refer to the capability of transferring an acyl group in a carboxylic acid or a salt thereof to an ε-position amino group more specifically than an α-position amino group in L-lysine. Specifically, the percentage of Nε-acyl-L-lysine produced by this protein activity, "(the production amount of Nε-acyl-L-lysine/the total production amount of Nα-acyl-L-lysine and Nε-acyl-L-lysine)×100(%)" is 60% or higher, 70% or higher, 80% or higher, 90% or higher, 95% or higher, 96% or higher, 97% or higher, 98% or higher, 99% or higher, or 99.5% or higher, for example, than without this protein activity.

In addition, the protein as described herein has excellent stability, such as storage stability in solutions, temperature stability, and pH stability. Specifically, even after being stored for a long time, such as 40 days, at 4° C. to 25° C. in an aqueous solution, the protein can maintain an activity of, for example, about 70% or higher, about 80% or higher, about 90% or higher, about 95% or higher, or about 100%, relative to the activity before storage. In addition, even after being incubated for a sufficient period of time, such as 1 hour, in an aqueous solution, such as a buffer, at a high temperature, such as about 50° C. or higher, about 60° C. or higher, about 70° C. or higher, or about 80° C. or higher (typically about 50° C. to 80° C.), the protein can maintain an activity of, for example, about 60% or higher, about 70% or higher, about 80% or higher, about 90% or higher, about 95% or higher, or about 100%, relative to activity before the incubation. Furthermore, even after being incubated for a sufficient period of time, such as 1 hour, in an aqueous solution, such as a buffer, with a low pH, such as a pH of about 6.5 or lower, about 6.0 or lower, about 5.5 or lower, about 5.0 or lower, about 4.5 or lower, or about 4.0 or lower (typically a pH of about 4.0 to 6.5), the protein can maintain an activity of, for example, about 60% or higher, about 70% or higher, about 80% or higher, about 90% or higher, about 95% or higher, or about 100%, relative to activity before the incubation. Consequently, the method as described herein has the advantage that it is excellent in long-term reactivity and can be carried out at wide ranges of temperature and pH.

The protein as described herein further has the characteristic of being excellent in resistance to heat treatment. Specifically, the protein has the advantages that, even after being incubated for a sufficient period of time, such as 0.5 hour to 1 hour, in heat treatment at a high temperature that can kill microorganisms such as in an aqueous solution, such as a buffer, at about 60° C. or higher, about 70° C. or higher, or about 80° C. or higher, it can maintain an activity of, for example, about 60% or higher, about 70% or higher, about 80% or higher, about 90% or higher, about 95% or higher, or about 100%, relative to activity before the incubation. Consequently, even after the microorganisms producing the protein are killed by the heat treatment, the protein produced by the microorganisms is not inactivated in the heat treatment solution, and the heat treatment solution can be favorably used for the reaction. This advantage is desirable also from the viewpoints of environmental safety and simplification of processes in that an enzymatic solution for use in the reaction can be easily prepared and sterilized.

In addition, the protein as described herein has the characteristic of being capable of exhibiting high activity under weak acid conditions. Under weakly acidic conditions, the reaction solution separates into an aqueous layer containing the L-lysine or a salt thereof and an oil layer containing the carboxylic acid or a salt thereof, and thus the viscosity of the reaction solution is likely to decrease. In contrast, under neutral conditions, the reaction solution does not separate into two layers, and the carboxylic acid or a salt thereof can emulsify, and thus the viscosity of the reaction solution is likely to increase. To obtain a Nε-acyl-L-lysine crystal having favorable properties and characteristics, such as a crystal having a short diameter, a low-viscosity reaction solution is preferred. The protein exhibits high activity under weakly acidic conditions, and thus the method as described herein can employ a low-viscosity reaction solution and does not need to carry out the reaction under conditions under which the carboxylic acid or a salt thereof would emulsify, such as under neutral conditions. Consequently, the method has the advantageous properties and characteristics that improve the Nε-acyl-L-lysine crystal.

The protein can further have the characteristic of being resistant to inhibition by a substrate at a high concentration. Specifically, the protein sufficiently catalyzes the reaction of the carboxylic acid or a salt thereof and L-lysine or a salt thereof to produce Nε-acyl-L-lysine, even when the concentration of the substrate is about 500 mM or higher, about 600 mM or higher, about 700 mM or higher, about 800 mM or higher, about 900 mM or higher, or about 1,000 mM or higher (typically about 500 mM to 1,000 mM), for example. Consequently, the method as described herein can use a substrate at a high concentration and can thus have the advantage that a large amount of Nε-acyl-L-lysine can be produced.

One or more mutations may be introduced within a catalytic domain and/or a part other than a catalytic domain in the protein so long as the target characteristic can be maintained. The position of a mutation that can maintain the target characteristics would be evident to persons of ordinary skill in the art. Specifically, those having ordinary skill in the art can 1) compare the amino acid sequences of a plurality of proteins having a similar kind of characteristic, 2) identify relatively conserved region(s) and relatively non-conserved region(s), and 3) predict region(s) that are important for the protein's functions, and region(s) that are not important for protein's functions based on the relatively conserved region(s) and the relatively non-conserved region(s), respectively, and can thus identify structural and functional correlation. Consequently, those of ordinary skill in the art can determine the position of the amino acid residue(s) which can withstand mutation while maintaining function in the amino acid sequence of the protein as described herein.

When the amino acid residue is mutated by substitution, the substitution of the amino acid residue may be conservative substitution. The term "conservative substitution" can refer to substituting a certain amino acid residue with an amino acid residue having a similar side chain. Families of the amino acid residue having a similar side chain are well known in the art. Examples of the families include amino acids having a basic side chain, such as lysine, arginine, and histidine, amino acids having an acidic side chain, aspartic acid and glutamic acid), amino acids having a non-charged polar side chain, such as asparagine, glutamine, serine, threonine, tyrosine, and cysteine, amino acids having a nonpolar side chain, such as glycine, alanine, valine, leucine, isoleucine, proline, phenylalanine, methionine, and tryptophan, amino acids having a β-position branched side chain, such as threonine, valine, and isoleucine, amino acids having an aromatic side chain, such as tyrosine, phenylalanine, tryptophan, and histidine, amino acids having a hydroxy group, such as alcoholic and phenolic-containing side chain, such as serine, threonine, and tyrosine, and amino acids having an sulfur-containing side chain, such as cysteine and methionine. The conservative substitution of the amino acid may be substitution between aspartic acid and glutamic acid, substitution among arginine, lysine, and histidine, substitution between tryptophan and phenylalanine, substitution between phenylalanine and valine, substitution among leucine, isoleucine, and alanine, and substitution between glycine and alanine.

In addition, the protein as described herein may be a fusion protein linked to a heterologous part via a peptide bond. Examples of the heterologous part can include peptide components that facilitate the purification of a target protein, such as tag parts, for example, a histidine tag or a Strep tag II; proteins used for the purification of the target protein, including glutathione-S-transferase and maltose binding proteins, peptide components that improve the solubility of the target protein, such as Nus-tag, peptide components working as chaperons, such as trigger factors, peptide components having other functions, such as a full-length protein or part thereof, and linkers.

Examples of the protein as described herein can include proteins derived from or native to bacteria belonging to the genus *Rhodothermus*, or more specifically, *Rhodothermus marinus*, naturally occurring homologues thereof, and artificially prepared mutant proteins. The mutant proteins can be obtained by introducing mutation into DNA encoding the target protein and producing the mutant protein using the obtained mutant DNA, for example. Examples of a method for introducing mutation can include site-directed mutagenesis and random mutation introduction treatment, such as treatment with a mutation agent and ultraviolet irradiation.

In one embodiment, the method as described herein can be carried out using the protein itself as described herein. For the protein as described herein, natural proteins or recombinant proteins can be used. The recombinant proteins can be obtained, for example, by using a cell-free vector or from the microorganisms producing the protein as described herein. The protein as described herein can be non-purified, roughly purified, or purified. These proteins may be used as an immobilized protein which is immobilized to a solid phase in the reaction.

The protein as described herein can be isolated by a known method and can be further purified depending on the circumstances, whereby the target protein is obtained. The microorganisms producing the protein can be a transformant. When a transformant is used, the target protein is obtained as an inactive target protein aggregate, that is, a protein inclusion body, which can be activated by an appropriate method. After the activation, the target protein may be obtained by separating and purifying the activated protein by a known method.

A medium for culturing the microorganisms is known, and can include a carbon source, a nitrogen source, a vitamin source, or the like and may be added to a nutrient medium such as LB medium or a minimal medium such as M9 medium. The transformant can be cultured at usually 16° C. to 42° C., or 25° C. to 37° C. for 5 hours to 168 hours, or 8 hours to 72 hours in accordance with the chosen host. Both shaking culture and stationary culture can be performed depending on the host; stirring and ventilation may be performed as needed. When an actinomycete is used as the expression host, conditions that can be used for producing the target protein can be used as appropriate. When an inducible promoter is used for the expression of the target protein, the culture can also be performed with a promoter inducer added to the medium.

The target protein can be purified and isolated from an extract of the transformant by the known method salting-out, sedimentation, such as isoelectric sedimentation, and solvent sedimentation, methods using difference in molecular weight such as dialysis, ultrafiltration, and gel filtration, methods using specific affinity such as ion-exchange chromatography, methods using difference in the degree of hydrophobicity such as hydrophobic chromatography and reversed phase chromatography, affinity chromatography, SDS polyacrylamide electrophoresis, isoelectric focusing, or combinations thereof. When the target protein is secreted, bacteria can be removed from the culture solution after culturing by centrifugation or the like to obtain a culture supernatant containing the target protein. The target protein can be purified and isolated also from this culture supernatant.

After the end of the culture of the transformant, the bacteria collected by centrifugation are suspended in a bacteria crushing buffer (20 mM to 100 mM of Tris-HCl (pH 8.0) and 5 mM of EDTA), and ultrasonic crushing is performed for about 10 minutes, whereby the bacteria can be crushed, for example. The bacteria crushing can also be performed with a solvent such as toluene added to the culture solution. This crushing treatment solution is centrifuged at 12,000 rpm for 10 minutes, whereby the purification operation described above can be performed on the supernatant. The sediment after the centrifugation can be solubilized with guanidinium chloride, urea, or the like to be further purified as needed. When the target protein is secreted, after the end of the culture of the transformant, the culture solution is centrifuged at 12,000 rpm for 10 minutes, whereby the purification operation described above can be performed on the supernatant.

Specifically, the purification of the target protein can be performed as follows, for example. After the end of the culture of the host, ammonium sulfate (2.8 M) is added to the culture supernatant or a cell extract to perform sedimentation fractionation, and then CM Sephadex C-50 or DEAE-Sephadex A-50 ion-exchange column chromatography or Octyl-Sepharose CL-4B or Phenyl-Sepharose CL-4B column chromatography, for example, can be further performed, whereby the target protein can be purified to the extent that a single band appears on a gel when polyacrylamide gel electrophoresis is performed thereon.

The activity of the obtained target protein can be evaluated by measuring Nε-acyl-L-lysine-specific aminoacylase activity or Nε-acetyl-L-lysine hydrolysis activity. For example, 1 U (unit) of the enzyme as described herein can be defined as an enzyme amount required for hydrolyzing 1 μmol of Nε-acetyl-L-lysine per 1 hour when incubation (50 mM of Tris-HCl buffer, pH 8.0) is performed at 37° C. with an Nε-acetyl-L-lysine solution as a substrate, and isolated L-lysine is quantified.

In another embodiment, the method as described herein can be carried out using the microorganisms producing the protein as described herein or a treatment solution thereof. Examples of the microorganisms producing the protein as described herein can include microorganisms naturally producing the protein, such as bacteria belonging to the genus *Rhodothermus*, and transformants. A transformant or a treatment solution thereof can be used.

For the treatment solution of the microorganisms producing the protein as described herein, a treatment solution containing the target protein and treated by any method can be used. Examples of the treatment can include the methods referred to in the isolation and purification described above, and a microbicidal treatment method that enables the killing of microorganisms. For the microbicidal treatment method, any method that enables the killing of microorganisms can be used; examples thereof can include heat treatment, acid treatment, alkaline treatment, surfactant treatment, and organic solvent treatment. The protein as described herein is excellent in resistance to heat treatment and treatment in low pH and high pH conditions, and a heat treatment solution, an acid treatment solution, and an alkaline treatment solution can be used for the treatment solution. The protein as described herein is excellent in heat treatment in particular, and the heat treatment solution is particularly preferably for the treatment solution. Examples of the heat treatment can include a heat treatment condition under a high temperature condition that enables the killing of microorganisms. Specific examples of the heat treatment condition can include incubation for a sufficient period of time, such as 0.5 hour to 1 hour, in an aqueous solution, such as a buffer, at about 60° C. or higher, about 70° C. or higher, or about 80° C. or higher.

The transformant as described herein can be a host cell that includes an expression unit having a polynucleotide encoding any of the proteins as described herein, and a promoter operably linked thereto.

The transformant as described herein can also be a host cell that includes an expression unit having a polynucleotide as described herein and a promoter operably linked thereto, such as (a) a polynucleotide including a nucleotide sequence of SEQ ID NO: 2 or 3; (b) a polynucleotide having 70% or higher homology with a nucleotide sequence of SEQ ID NO: 2 or 3, and encoding a protein having Nε-acyl-L-lysine-specific aminoacylase activity; (c) a polynucleotide that is able to hybridize with a polynucleotide including a nucleotide sequence complementary to the nucleotide sequence of SEQ ID NO: 2 or 3 under stringent conditions and encoding a protein having Nε-acyl-L-lysine-specific aminoacylase activity; and (d) a degenerate variant of the polynucleotide as described above.

These polynucleotides may be DNA or RNA and can be DNA. The nucleotide sequence of SEQ ID NO: 2 or 3 encodes the amino acid sequence of SEQ ID NO: 1.

The homology percentage of the nucleotide sequence relative to the nucleotide sequence of SEQ ID NO: 2 or 3 can be 70% or higher, 75% or higher, 80% or higher, 85% or higher, 90% or higher, 91% or higher, 92% or higher, 93% or higher, 94% or higher, 95% or higher, 96% or higher, 97% or higher, 98% or higher, or 99% or higher.

The term "stringent conditions" can refer to conditions in which a specific hybrid is formed, and a non-specific hybrid is not formed. Examples of the stringent conditions can include hybridization at about 45° C. in 6×SSC (sodium chloride/sodium citrate) followed by washing once or twice or more at 50° C. to 65° C. in 0.2×SSC and 0.1% SDS.

The term "degenerate variant" can refer to a polynucleotide mutant in which at least one codon encoding a certain amino acid residue has been changed into another codon encoding the same amino acid residue. This degenerate variant is a mutant based on silent mutation, and a protein encoded by the degenerate variant is the same as a protein encoded by the polynucleotide before being varied.

The degenerate variant can be a polynucleotide mutant in which the codon has been changed so as to be adapted to the codon usage frequency of the chosen host cell to which the degenerate variant is to be introduced. When a gene is expressed by a heterologous host cell, for example, microorganisms, a corresponding tRNA molecular species can be present in insufficient amounts due to a difference in codon frequency, which may cause a reduction in translation efficiency and/or incorrect translation, such as the stop of translation. In *Escherichia coli*, for example, known low frequency codons are listed in Table 1.

TABLE 1

Low frequency codons in *Escherichia coli*

| Amino acid residue | Codon | low frequency codons |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Given these circumstances, the degenerate variant can be adapted to the codon usage frequency of a host cell described below. In the degenerate variant as described herein, for example, a codon encoding one or more of the amino acid residues arginine, glycine, isoleucine, leucine, and proline may be changed. More specifically, in the degenerate variant, one or more kinds of the low frequency codons such as AGG, AGA, CGG, CGA, GGA, AUA, CUA, and CCC may be changed. The degenerate variant may contain one or more changes such as one, two, three, four, or five, codons as described below:

i) A change of at least one codon of AGG, AGA, CGG, and/or CGA encoding Arg into another codon, such as CGU or CGC encoding Arg;

ii) A change of one codon (GGA) encoding Gly into another codon (GGG, GGU, or GGC);

iii) A change of one codon (AUA) encoding Ile into another codon (AUU or AUC);

iv) A change of one codon (CUA) encoding Leu into another codon (UUG, UUA, CUG, CUU, or CUC); and v) A change of one codon (CCC) encoding Pro into another codon (CCG, CCA, or CCU).

When the degenerate variant is RNA, the nucleotide residue "U" should be used as described above, whereas when the degenerate variant is DNA, "T" should be used in place of the nucleotide residue "U." The number of mutations of nucleotide residues that can be adapted to the codon usage frequency of the host cell is not limited so long as the same protein is encoded before and after mutation, and can be, for example, 1 to 500, 1 to 400, 1 to 300, 1 to 200, or 1 to 100.

The low frequency codon can be easily identified based on the type and genome sequence information of any host cell by using techniques known in the art. Consequently, the degenerate variant may contain a change of a low frequency codon into a non-low frequency codon, such as a high frequency codon. Methods for designing mutants consider not only the low frequency codon(s), but also the known adaptability to the genome GC content of the chosen strain (Alan Villalobos et al., Gene Designer: a synthetic biology tool for constructing artificial DNA segments, BMC Bioinformatics. 2006 Jun. 6; 7: 285). Thus, the mutant described above can be prepared as appropriate in accordance with the chosen host cell, such as those microorganisms described below, to which the mutant can be introduced.

The term "expression unit" can refer to a minimum unit that contains a certain polynucleotide to be expressed as a protein and a promoter operably linked thereto, and enables the transcription of the polynucleotide and eventually the production of the protein encoded by the polynucleotide. The expression unit may further contain elements such as a terminator, a ribosome binding site, and a drug-resistant gene. The expression unit may be DNA or RNA and can be DNA. The expression unit may be homologous or heterologous relative to the host cell and can be a heterologous expression unit.

The expression unit may be homologous or heterologous relative to the host cell and can be a heterologous expression unit. The term "heterologous expression unit" can mean that the expression unit is heterologous relative to the host cell. Consequently, at least one element in the expression unit can be heterologous relative to the host cell. Examples of such a heterologous element relative to the host cell can include the elements described above. Either one or both of the polynucleotide encoding the target protein and the promoter contained in the heterologous expression unit can be heterologous relative to the host cell. Consequently, either one or both of the polynucleotide encoding the target protein and the promoter are derived from a living body other than the host cell, such as a prokaryote or a eukaryote, a microorganism, an insect, a plant, or an animal such as a mammal, or a virus or are artificially synthesized. Alternatively, the polynucleotide encoding the target protein may be heterologous relative to the host cell. The target protein can be heterologous relative to the host cell.

The promoter in the heterologous expression unit is not limited to a particular promoter so long as it can express the protein encoded by the polynucleotide linked downstream of the promoter in the host cell. The promoter may be homologous or heterologous relative to the host cell, for example. Constitutive or inducible promoters generally used for the production of recombinant proteins can be used, for example. Examples of such a promoter can include the PhoA promoter, the PhoC promoter, the T7 promoter, the T5 promoter, the T3 promoter, the lac promoter, the trp promoter, the trc promoter, the tac promoter, the PR promoter, the PL promoter, the SP6 promoter, arabinose-inducible promoters, cold shock promoters, and tetracycline-inducible promoters. A promoter having strong transcription activity in the host cell can be used. Examples of the promoter having strong transcription activity in the host cell can include promoters of genes highly expressed in the host cell and promoters derived from viruses. When coryneform bacteria are selected as the host cell, the cspB promoter or the like can be suitably used.

Examples of the host cell can include various kinds of microorganisms including *E. coli*, actinomycetes, and coryneform bacteria. When *E. coli* is used as the host cell, strains often used for cloning and the expression of heterologous proteins, such as HB101, MC1061, JM109, CJ236, and MV1184, can be used. When actinomycete is used as the host cell, strains often used for the expression of heterologous proteins, such as *S. lividans* TK24 and coelicolor A3(2), can be used. When coryneform bacterium is used as the host cell, aerobic gram-positive bacillus can be used, which includes bacteria currently consolidated into the genus *Corynebacterium*, although conventionally classified into the genus *Brevibacterium* (Int. J. Syst. Bacteriol., 41, 255 (1981)), and also includes bacteria belonging to the genus *Brevibacterium*, which is extremely closely related to the genus *Corynebacterium*. The advantages of coryneform bacterium can include the capability of simplifying and omitting its purification process when the target protein is secreted. This is because the amount of the protein extracellularly secreted is intrinsically extremely small as compared to mold, yeast, and bacteria belonging to the genus Bacillus, which have been considered to be suitable for protein secretion. Other advantages include the capability of reducing impurities and side reactions caused by bacterial components, impure enzymes, and the like because the culture supernatant can be used as an enzyme source when the enzyme reaction is carried out using a secreted enzyme. Finally, other advantages include the low cost of the medium, and the ease of growing using a simple medium containing sugars, ammonia, inorganic salts, or the like so simplifying the method of culture, and improving culture productivity. Using the Tat-system secretion pathway, industrially useful proteins such as isomaltodextranase and glutaminase, which are difficult to produce by secretion using the previously known Sec-system secretion pathway, can also be efficiently secreted (WO 2005/103278). The target protein as described herein can also be extracellularly secreted using an appropriate secretion pathway such as the Tat-system secretion pathway. The "Tat-system" is a pathway also called the "Twin-arginine-translocation-pathway" and means a mechanism or pathway that recognizes a storage region of arginine-arginine stored in a signal peptide to secrete a protein by a membrane protein containing TatA, B, C, and E. Examples of the Tat-system signal peptide can include the signal peptide of trimethylamine N-oxidoreductase (TorA) native to *E. coli*. Examples of coryneform bacteria can include the following:

*Corynebacterium acetoacidophilum,*
*Corynebacterium acetoglutamicum,*
*Corynebacterium alkanolyticum,*
*Corynebacterium callunae,*
*Corynebacterium glutamicum,*
*Corynebacterium lilium,*
*Corynebacterium melassecola,*
*Corynebacterium thermoaminogenes,*
*Corynebacterium herculis,*
*Brevibacterium divaricatum,*
*Brevibacterium flavum,*
*Brevibacterium immariophilum,*
*Brevibacterium lactofermentum,*
*Brevibacterium roseum,*
*Brevibacterium saccharolyticum,*
*Brevibacterium tiogenitalis,*
*Corynebacterium ammoniagenes,*
*Brevibacterium album,*
*Brevibacterium cerinum,* and
*Microbacterium ammoniaphilum.*

Specifically, the following strains can be exemplified.
*Corynebacterium acetoacidophilum* ATCC13870,
*Corynebacterium acetoglutamicum* ATCC15806,
*Corynebacterium alkanolyticum* ATCC21511,
*Corynebacterium callunae* ATCC15991,
*Corynebacterium glutamicum* ATCC13020, ATCC13032, ATCC13060, ATCC13869, and FERM BP-734,
*Corynebacterium lilium* ATCC15990,
*Corynebacterium melassecola* ATCC17965,
*Corynebacterium efficiens* AJ12340 (FERM BP-1539),

*Corynebacterium herculis* ATCC13868,
*Corynebacterium divaricatum* ATCC14020,
*Corynebacterium flavum* ATCC13826, ATCC14067, and AJ12418 (FERM BP-2205),
*Brevibacterium immariophilum* ATCC14068,
*Brevibacterium lactofermentum* ATCC13869,
*Brevibacterium roseum* ATCC13825,
*Brevibacterium saccharolyticum* ATCC14066,
*Brevibacterium tiogenitalis* ATCC19240,
*Corynebacterium ammoniagenes* ATCC6871 and ATCC6872,
*Brevibacterium album* 15111,
*Brevibacterium cerinum* ATCC15112, and
*Microbacterium ammoniaphilum* ATCC15354.

In particular, *Corynebacterium glutamicum* AJ12036 (refer to WO 02/081694), isolated as a Streptomycin (Sm) resistant mutant strain from the wild-type strain *Corynebacterium glutamicum* (*C. glutamicum*) ATCC13869, is predicted to have mutation in a functional gene affecting protein secretion, and its ability to secrete proteins under optimum culture conditions is about two to three times higher than that of its parent strain (wild-type strain), thus being suitable as a host bacterium.

Furthermore, when a strain used as the host is modified so as not to produce a native cell surface protein, target protein(s) secreted into the medium can be easily purified, which is particularly preferred. Such modification can be performed by introducing mutation to a cell surface protein or its expression regulation region on a chromosome by mutation or gene recombination. Examples of the coryneform bacterium modified so as not to produce the cell surface protein can include AJ12036 (refer to WO 01/23491), in which the cell surface protein PS2 is inactivated in the *C. glutamicum* YDK010 strain.

The transformant as described herein can be prepared by any method known in the art. An expression unit in the host cell can be incorporated into the genome of the host cell or can be present on an expression vector, for example. Transforming the host cell with the expression unit can be by any method known in the art, such as a competent cell method and an electroporation method. When the expression vector is an integrative vector that causes homologous recombination with the genome DNA of the host cell, the expression unit can be incorporated into the genome DNA of the host cell by transformation. In contrast, when the expression vector is a non-integrative vector that does not cause homologous recombination with the genome DNA of the host cell, the expression vector is not incorporated into the genome DNA of the host cell by transformation and remains in the host cell independent of the genome DNA. Alternatively, the expression unit can be incorporated into the genome of the host cell by a genome editing technique, such as the CRISPR/Cas system and Transcription Activator-Like Effector Nucleases (TALEN).

The expression vector as described herein may further contain elements such as a terminator that is able to function in the host cell, a ribosome binding site, and a drug-resistant gene, in addition to the minimum expression unit. Examples of the drug-resistant gene can include genes resistant to drugs such as tetracycline, ampicillin, kanamycin, hygromycin, and phosphinothricin.

The expression vector may further contain a region that enables homologous recombination with the genome of the host cell. The expression vector may be designed such that the expression unit is positioned between a pair of homologous regions, such as a homology arm loxP and FRT homologous to a specific sequence in the genome of the host cell, for example. The genome region, which is the target of the homologous region, of the host cell into which the expression unit is introduced, which is not limited to any particular region, may be a locus of a gene having a large amount of expression in the host cell.

The expression vector may be a plasmid, a virus vector, a phage, or an artificial chromosome. The expression vector may be an integrative vector or a non-integrative vector. The integrative vector may be of a type which the entirety is incorporated into the genome of the host cell. Alternatively, the expression vector may be of a type only part of which, such as the expression unit, is incorporated into the genome of the host cell. Furthermore, the expression vector may be a DNA vector or an RNA vector, such as a retrovirus. For the expression vector, generally used expression vectors may be used. Examples of such expression vectors can include pUC, such as pUC19 and pUC18, pSTV, pBR, such as pBR322, pHSG, such as pHSG299, pHSG298, pHSG399, and pHSG398, RSF, such as RSF1010, pACYC, such as pACYC177 and pACYC184, pMW, such as pMW119, pMW118, pMW219, and pMW218, pQE, such as pQE30, and derivatives thereof. When a coryneform bacterium such as *Corynebacterium glutamicum* is selected as the host cell, the high copy vector pPK4 or the like can be suitably used.

As described above, the method as described herein can be carried out in a reaction system including the carboxylic acid or a salt thereof and L-lysine or a salt thereof in the presence of the protein by itself and/or the microorganisms producing the protein, or a treatment solution containing the microorganisms producing the protein.

For the carboxylic acid, any carboxylic acid that can supply an acyl group for the reaction with the ε-position amino group of L-lysine can be used. Examples of such a carboxylic acid can include linear or branched, saturated or unsaturated aliphatic acids and aromatic carboxylic acids having saturated or unsaturated side chains. The carbon number of such a carboxylic acid can be five or more, or eight or more. The carbon number of the carboxylic acid may be, for example, 30 or less, 25 or less, or 20 or less. More specifically, examples of the carboxylic acid used in the method as described herein can include octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), linoleic acid, oleic acid, benzoic acid, methoxymethyl benzoic acid, phenylpropionic acid, cinnamoyl acid, methoxy cinnamoyl acid, linolenic acid, and/or cinnamic acid. Octanoic acid and dodecanoic acid are particular examples.

For the salt of the carboxylic acid or L-lysine, any salt can be used. Examples of such a salt can include nonmetallic and metallic salts. Nonmetallic salts can include inorganic acid salts, for example, hydrochlorides; inorganic basic salts, for example, ammonium salts; organic acid salts, for example, acetates; and organic basic salts, for example, triethylamine salts. Metallic salts can include alkali metal salts, for example, sodium salts and potassium salts; and alkaline earth metal salts, for example, calcium salts and magnesium salts.

The concentration of a substrate, the carboxylic acid or a salt thereof, and/or the L-lysine or a salt thereof in the reaction system is not limited to a particular concentration so long as the production of Nε-acyl-L-lysine by the protein is enabled; the concentration may be, for example, 1 mM or higher, 10 mM or higher, or 100 mM or higher. The protein as described herein has the characteristic of being resistant to inhibition by a substrate present in a high concentration, and the carboxylic acid or a salt thereof and L-lysine or a salt thereof can be sufficiently reacted to produce Nε-acyl-L-lysine even with a substrate concentration such as about 500 mM or higher, about 600 mM or higher, about 700 mM or higher, about 800 mM or higher, about 900 mM or higher, or about 1,000 mM or higher, typically about 500 mM to 1,000 mM. Consequently, the method as described herein can use a substrate at a high concentration and thus has the advantage that a large amount of Nε-acyl-L-lysine can be produced. Either L-lysine or a salt thereof or the carboxylic acid or a salt thereof may be present in the reaction system in an excessive amount as the substrate. If the amount of substrate becomes insufficient during the reaction, more substrate can be added as needed.

The reaction temperature in the method as described herein is not limited to a particular temperature so long as the production of Nε-acyl-L-lysine by the protein is enabled; the reaction can be carried out under a temperature of about 4° C. to 80° C., for example. The protein as described herein is stable at high temperatures, and the reaction can be carried out under a temperature condition of about 50° C. or higher, about 60° C. or higher, about 70° C. or higher, or about 80° C. or higher, typically about 50° C. to 80° C., for example.

The pH in the method as described herein is not limited to a particular value so long as the production of Nε-acyl-L-lysine by the protein is enabled; the reaction can be carried out at a pH of about 4.0 to 11.0, for example. The protein as described herein is stable at low pH in particular, and the reaction may be carried out at a pH of about 6.5 or lower, about 6.0 or lower, about 5.5 or lower, about 5.0 or lower, about 4.5 or lower, or about 4.0 or lower, typically a pH of about 4.0 to 6.5, for example.

In the method as described herein, the reaction may be carried out in the reaction solution with a non-emulsified solution of the carboxylic acid or a salt thereof. In general, at a lower pH, the reaction solution separates into an aqueous layer containing the L-lysine or a salt thereof and an oil layer containing the carboxylic acid or a salt thereof, whereas at a higher pH, the oil layer dissolves in the aqueous layer to give a transparent reaction solution. However, at an intermediate pH between the high and low pH values, the oil layer of the reaction solution can be emulsified, and the viscosity of the reaction solution is likely to increase. To obtain a Nε-acyl-L-lysine crystal having favorable properties and characteristics, such as a short diameter crystal, a non-emulsified reaction solution with low viscosity can be used. The conditions to achieve a non-emulsified solution of the carboxylic acid or a salt thereof varies with the type of the carboxylic acid or a salt thereof. For example, with octanoic acid, the pH should be 5.5 or lower to obtain a non-emulsified solution, that is, separated into two layers, or should be 6.8 or higher to obtain a transparent reaction solution. Therefore, a pH of at least 5.5 and lower than 6.8 will result in an emulsified solution. With dodecanoic acid, the pH should be 6.2 or lower to obtain a non-emulsified solution, that is, separated into two layers, or the pH should be 7.5 or higher to obtain a transparent reaction solution. Therefore, a pH of at least 6.2 and lower than 7.5 will result in an emulsified solution. Those skilled in the art can achieve a non-emulsified solution by adjusting the pH of the reaction system as appropriate and in accordance with the type of the carboxylic acid or a salt thereof. The reaction can be carried out as appropriate so to obtain a non-emulsified solution; the reaction may be carried out so to obtain a non-emulsified solution with a pH of 6.8 or higher when octanoic acid is used as the carboxylic acid, and at a pH of 6.2 or lower when dodecanoic acid is used as the carboxylic acid. When the reaction carried out so that the solution of carboxylic acid or a salt thereof is non-emulsified, the properties and characteristics, such as a short crystal diameter of Nε-acyl-L-lysine, can be improved.

The reaction time can be set as appropriate. The protein as described herein can maintain its activity to a higher degree even after long-term storage, for example, 40 days and can thus be used in a long-term reaction and eventually the production of a large amount of Nε-acyl-L-lysine.

For the reaction system, when the protein itself or the treatment solution is used, for example, an aqueous solution such as a buffer can be used. When the microorganisms producing the protein are used, the reaction can be carried out by culturing the microorganisms in any medium such as a liquid medium. In this case, the culture temperature can be, for example, 15° C. to 42° C., or 20° C. to 37° C. The culture of the host cell can be performed, for example, at pH 5.5 to 8.5, or pH 6 to 8. Under these conditions, the host cell sufficiently grows, and the protein can be obtained in a large amount. The culture may be performed by a known method of fermentation such as a batch culture, a feeding culture, or a continuous culture. For the liquid medium, any liquid medium used for the culture of the host cell can be used. The liquid medium can contain carbohydrates such as glucose, fructose, glycerol, and starch as a carbon source. The liquid medium can contain an inorganic or organic nitrogen source, such as ammonium sulfate, ammonium chloride, a hydrolysate of casein, a yeast extract, polypeptone, and bactotryptone. The liquid medium can further contain other nutrient sources such as inorganic salts, such as sodium diphosphate, potassium diphosphate, dipotassium hydrogenphosphate, magnesium chloride, magnesium sulfate, and calcium chloride, vitamins, such as vitamin B1, and antibiotics.

For the reaction system, an aqueous solvent can be suitably used. In particular, when the carboxylic acid has a relatively long chain and the reaction is carried out in the aqueous solvent, the Nε-acyl-L-lysine that is produced is insoluble or poorly soluble in water and thus precipitates easily from the reaction system; consequently, the synthesis reaction of Nε-acyl-L-lysine proceeds more conspicuously, more preferentially, and more efficiently than the reverse degradation reaction of Nε-acyl-L-lysine. In this case, the synthesized Nε-acyl-L-lysine quickly separates from the aqueous phase and can thus be collected extremely easily. For example, the separated Nε-acyl-L-lysine can be directly collected, or Nε-acyl-L-lysine can be extracted and collected from an aqueous reaction system easily by an organic solvent. When Nε-acyl-L-lysine is produced by the method as described herein, a carboxylic acid having a relatively long chain can be selected, for example, based on solubility in the aqueous solvent. The "aqueous solvent" can include water. Even when the reaction is carried out in an aqueous solvent, the oil layer, that is, the an organic solvent layer, can be separately overlaid, thereby enabling a two-phase, or the aqueous solvent/the organic solvent, reaction.

EXAMPLES

The present invention is explained in more detail with reference to the following non-limiting examples.

Example 1: Production of Aminoacylase Native to *Rhodothermus marinus* (RmELA) by *C. glutamicum*

1-1) Construction of Vector (pPK5) Obtained by Modifying NaeI Recognition Site in pPK4 Vector In pPK4 described in Japanese Patent Application Laid-open No. H09-322774, one recognition sequence of the restriction enzyme NaeI is present. To modify this sequence, primers of SEQ ID NO: 4 and SEQ ID NO: 5 that include a sequence in which the NaeI recognition sequence gccggc was modified to gcaggc and its surrounding pPK4 sequence were synthesized. Next, with pPK4 as a template, using the primers of SEQ ID NO: 4 and SEQ ID NO: 5, the full plasmid length with about 5.6 kbp was amplified by the PCR method. For PCR, Pyrobest (registered trademark) DNA polymerase (Takara Bio) was used, in which the reaction conditions were in accordance with a protocol recommended by the manufacturer.

The obtained PCR product was treated with the restriction enzyme DpnI to digest a methylated template DNA. A non-methylated plasmid obtained after DpnI digestion was introduced into a competent cell of E. coli JM109 (Takara Bio) to acquire a plasmid. It was revealed from nucleotide sequencing that a plasmid with the NaeI recognition site modified was constructed as expected. The determination of the nucleotide sequence was performed using BigDye (registered trademark) Terminator v3.1 Cycle Sequencing Kit (Applied Biosystems) and 3130 Genetic Analyzer (Applied Biosystems). The thus obtained vector with the NaeI recognition site was designated as pPK5.

(SEQ ID NO: 4)
5'-cgagccaccaggcaggcgggaaaatcg-3'

(SEQ ID NO: 5)
5'-cgattttcccgcctgcctggtggctcg-3'

1-2) Construction of Vector in which tatABC Gene is included in pPK5 Vector (pPK5-tatABC)

Next, with pVtatABC, which is an amplified plasmid of a Tat-system secretion system described in WO 2005/103278, as a template, using primers of SEQ ID NO: 6 and SEQ ID NO: 7, a DNA fragment with about 3.7 kbp including a sequence encoding the tatABC gene was amplified by the PCR method. The primer of SEQ ID NO: 7 is designed to add the recognition sequences of the restriction enzymes KpnI and ApaI to the 5' end side of a nucleotide sequence complementary to pVtatABC.

The end of the obtained PCR product was phosphorylated using BKL Kit (Takara Bio) and was ligated with the pPK5 vector that was separately treated with KpnI, and was further blunted using BKL Kit (Takara Bio), and the end of which was further dephosphorylated using CIAP (Takara Bio). For the ligation reaction, DNA Ligation Kit Ver. 2.1 (Takara Bio) was used, in which the reaction condition was in accordance with a protocol recommended by the manufacturer. The obtained ligation product was introduced into a competent cell of E. coli JM109 (Takara Bio) to acquire a plasmid. It was revealed from the nucleotide sequencing of an inserted fragment that an expected gene was inserted. The thus obtained vector including the tatABC gene in the pPK5 vector was designated as pPK5-tatABC.

(SEQ ID NO: 6)
5'-cccgcttgatcattcctttaagg-3'

(SEQ ID NO: 7)
5'-aatgggcccttggtaccccctaaataatatcggtcc-3'

1-3) Construction of Vector obtained by modifying KpnI and XbaI Recognition Sites within tatABC gene in pPK5-tatABC Vector (pPK6)

In the tatABC gene region within the pPK5-tatABC vector constructed in 1-2), one recognition sequence for each of the restriction enzymes KpnI and XbaI is present. To modify these sequences, primers described in SEQ ID NO: 8 and SEQ ID NO: 9 including a sequence with the KpnI recognition sequence ggtacc modified to ggaacc and its surrounding sequence in pPK5-tatABC and primers described in SEQ ID NO: 10 and SEQ ID NO: 11 including a sequence with the XbaI recognition sequence tctaga modified to tgtaga and its surrounding sequence in pPK5-tatABC were synthesized.

First, with pPK5-tatABC as a template, using the primers of SEQ ID NO: 8 and SEQ ID NO: 9, full plasmid length with about 9.4 kbp was amplified by the PCR method so as to modify the KpnI recognition site within the tatABC gene region.

The obtained PCR product was treated with the restriction enzyme DpnI to digest a methylated template DNA. A non-methylated plasmid obtained after DpnI digestion was introduced to a competent cell of E. coli JM109 (Takara Bio) to acquire a plasmid. It was revealed from nucleotide sequencing that modification to an expected gene was performed. The thus obtained vector with the KpnI recognition site within the tatABC gene region in the pPK5-tatABC vector modified was designated as pPK5-tatABCΔKpnI.

Next, with pPK5-tatABCΔKpnI as a template, using primers of SEQ ID NO: 10 and SEQ ID NO: 11, full plasmid length with about 9.4 kbp was amplified by the PCR method so as to modify the XbaI recognition site within the tatABC gene region.

The obtained PCR product was treated with the restriction enzyme DpnI to digest a methylated template DNA. A non-methylated plasmid obtained after DpnI digestion was introduced to a competent cell of E. coli JM109 (Takara Bio) to acquire a plasmid. It was revealed from nucleotide sequencing that modification to an expected gene was performed. The thus obtained vector with the KpnI and XbaI recognition sites within the tatABC gene region in the pPK5-tatABC vector modified was designated as pPK6.

(SEQ ID NO: 8)
5'-cgtgctctaggggaaccgtgcgttccc-3'

(SEQ ID NO: 9)
5'-gggaacgcacggttcccctagagcacg-3'

(SEQ ID NO: 10)
5'-cgacgctgaagttgtagagatcatccg-3'

(SEQ ID NO: 11)
5'-cggatgatctctacaacttcagcgtcg-3'

1-4) Construction of Plasmid Coexpressing tatABC Gene and Gene Encoding RmELA with TorA Signal Sequence Added (pPK6-RmELA)

DNA with the KpnI recognition sequence (ggtacc), a promoter region of the cspB gene native to C. glutamicum ATCC13869, a TorA signal sequence native to E. coli W3110, a gene encoding amidohydrolase native to Rhodothermus marinus (NCBI; WP_012844854.1, SEQ ID NO: 1) (SEQ ID NO: 2), and the ApaI recognition site (gggccc) linked in this order was acquired by chemical synthesis (SEQ ID NO: 3). A gene encoding RmELA was designed so as to have an optimum codon in accordance with the codon usage frequency of C. glutamicum based on information disclosed in "Codon Usage Database" (kazusa.or.jp/codon; Nakamura, Y. et al, Nucl. Acids Res., 28, 292 (2000)).

Next, the obtained synthesized DNA was treated with the restriction enzymes KpnI and ApaI and was ligated with the pPK6 vector separately treated with KpnI and ApaI. The obtained ligation product was introduced to a competent cell of *E. coli* JM109 (Takara Bio) to acquire a plasmid. It was revealed from the nucleotide sequencing of an inserted fragment that an expected gene was inserted. The thus obtained coexpression plasmid of the tatABC gene encoding the Tat-system secretion system and the gene encoding RmELA with the TorA signal sequence added was designated as pPK6-RmELA.

1-5) Introduction of Plasmid to *C. glutamicum* WDK010 Strain

Using pPK6-RmELA constructed in 1-4), the WDK010 strain (WO 2010/067871) acquired from a mutant strain native to *C. glutamicum* ATCC13869 was transformed, and the transformant was selected in a CM2G agar medium (10 g of a yeast extract, 10 g of polypeptone, 5 g of glucose, 5 g of sodium chloride, 0.2 g of DL-methionine, 15 g of agar, pH 7.2, and filled up to 1 L with water) containing 25 mg/l of kanamycin. The obtained transformant was designated as a WDK010/pPK6-RmELA strain.

1-6) Expression of RmELA in *C. glutamicum* WDK010 Strain

A platinum loop of the WDK010/pPK6-RmELA strain was inoculated to a Sakaguchi flask test tube with a whole volume of 500 ml into which 50 ml of a seed liquid medium (10 g of a yeast extract, 10 g of polypeptone, 5 g of glucose, 0.1 g as a nitrogen amount of a soybean hydrolysate, 0.02 g of DL-methionine, pH 7.2, and filled up to 1 L with water) containing 25 mg/l of kanamycin had been put and was cultured with shaking at 30° C. for 8 hours. The thus obtained culture solution in an amount of 0.9 ml was added to a 1,000 ml jar fermenter into which 300 ml of a main liquid medium (120 g of glucose, 3 g of ammonium sulfate, 1.5 g of potassium dihydrogenphosphate, 0.2 g as a nitrogen amount of a soybean hydrolysate, 3 g of magnesium sulfate heptahydrate, 0.15 g of DL-methionine, 0.03 g of iron (II) sulfate heptahydrate, 0.03 g of manganese (II) sulfate pentahydrate, 0.04 g of zinc sulfate heptahydrate, 0.25 g of calcium chloride, 0.45 mg of thiamine hydrochloride, 0.45 mg of biotin, 0.1 ml of Disfoam GD-113K (manufactured by NOF Corporation), pH 6.2, and filled up to 1 L with water) containing 25 mg/l of kanamycin had been put to start main culture. The main culture was controlled at 30° C., a ventilation of 1/1 vvm, and pH 6.6 using ammonia and was performed until the glucose was consumed. Stirring was controlled at 500 rpm or higher so as to give a dissolved oxygen concentration of 5% or higher.

The obtained culture solution was centrifuged, and the supernatant was collected. The degradation activity of Nε-acetyl-L-lysine within this culture supernatant was measured; an activity of 21 U per 1 ml of the culture supernatant was detected.

Activity was measured with 40 mM Nε-acetyl-L-lysine and 50 mM Tris-HCl (pH 7.0) at 37° C., and the concentration of lysine produced along with the degradation of Nε-acetyl-L-lysine was measured. For the measurement of lysine, BF-5 and a lysine electrode (manufactured by Oji Scientific Instruments Co., Ltd.) were used. Here, 1 U was defined as an enzyme amount that releases 1 μmol lysine from Nε-acetyl-L-lysine (per 1 minute).

Example 2: Production of Aminoacylase Native to *Rhodothermus marinus* (RmELA) by *E. coli*

2-1) Preparation of RmELA *E. coli* Expression Strain

With pPK6-RmELA as a template, using primers of SEQ ID NO: 12 and SEQ ID NO: 13, a DNA fragment with about 1.7 kbp including a sequence encoding the RmELA gene was amplified by the PCR method. The primers of SEQ ID NO: 12 and SEQ ID NO: 13 are designed to add the recognition sequences of the restriction enzymes NdeI and XhoI, respectively, to the 5' end side of a nucleotide sequence complementary to the RmELA gene.

Next, the obtained PCR product was treated with the restriction enzymes NdeI and XhoI and was ligated with a plasmid vector pET-21a (Novagen) separately treated with NdeI and XhoI. The ligation product was introduced to a competent cell of *E. coli* JM109 (Takara Bio) to acquire a plasmid. It was revealed from the nucleotide sequencing of an inserted fragment that an expected gene was inserted. The thus obtained gene expression plasmid encoding RmELA based on the pET21a vector was designated as pET21a-RmELA.

Subsequently, the plasmid pET21a-RmELA was transformed into a competent cell of *E. coli* BL21 (DE3) (life technologies), and the transformant was selected in an LB medium containing 100 mg/l of ampicillin. The thus obtained RmELA *E. coli* expression strain was designated as a BL21 (DE3)/pET21a-RmELA strain.

```
                              (SEQ ID NO: 12)
    5'-aaaCATATGCTCCTCCTCCCTATGCAGGCA-3'

(SEQ ID NO: 13)
    5'-aaaaCTCGAGTGGGGAGGCCGGACACAGACCTGCTGC-3'
```

2-2) Expression of RmELA using *E. coli*

A platinum loop of the *E. coli* BL21 (DE3)/pET21a-RmELA strain was inoculated to a 500 ml Sakaguchi flask test tube into which 50 ml of Overnight Express Instant TB medium (Novagen) containing 100 mg/l of ampicillin had been put and was cultured with shaking at 37° C. for 24 hours.

When the degradation activity of Nε-acetyl-L-lysine was measured using the obtained culture solution, an activity of about 3.9 U per 1 ml of the culture solution was detected. In contrast, when a culture solution of an *E. coli* BL21 (DE3) strain transformed by a plasmid vector pET-21a (Novagegn) into which no RmELA gene had been inserted was used, no activity was detected.

Example 3: Purification of Aminoacylase Native to *Rhodothermus marinus* (RmELA)

A platinum loop of the BL21 (DE3)/pET21a-RmELA strain was inoculated into a 500 ml Sakaguchi flask into which 50 ml of Overnight Express Instant TB medium (Novagen) containing 100 mg/l of ampicillin had been put and was cultured with shaking at 37° C. for 24 hours.

The obtained culture solution was centrifuged, and the supernatant was removed to collect bacteria, which were washed with a physiological saline solution (0.85% NaCl) twice and was suspended in 10 ml of 25 mM Tris-HCl (pH 8.0) to obtain washed bacteria. The total activity of the obtained washed bacteria was 194 U.

Next, the washed bacteria were ultrasonically crushed, and the supernatant obtained by centrifugation was collected as an available protein solution. The total activity of the available protein solution was 147 U, and the specific activity thereof was 1 U/mg.

Subsequently, the available protein solution was subjected to heat treatment at 75° C. for 30 minutes, and the supernatant obtained by centrifugation was collected as a heated treatment solution. The total activity of the heated treatment solution was 158 U, and the specific activity thereof was 11 U/mg.

Furthermore, the heated treatment solution (actually measured pH 7.9) was supplied to an anion-exchange chromatography column HiTrap Q HP (manufactured by GE Healthcare Bioscience Corporation, CV=1 ml) equilibrated with 50 mM Tris-HCl (pH 8.0) and was eluted with an NaCl concentration gradient of 0 mM to 500 mM; an active fraction was eluted on a condition of about 250 mM. The total activity of the active fraction was 84 U, and the specific activity thereof was 15 U/mg.

Finally, this active fraction was concentrated using Amicon Ultra-15 30 k (manufactured by Millipore), was supplied to a gel filtration chromatography column Hiload 16/60 superdex 200 pg (manufactured by GE Healthcare Bioscience Corporation, CV=120 ml) equilibrated with 50 mM Tris-HCl (pH 8.0) and 150 mM NaCl to perform protein elution at a flow rate of 1 ml/min; the total activity of the active fraction was 38 U, and the specific fraction thereof was 28 U/mg. When this active fraction was subjected to polyacrylamide gel electrophoresis, it was revealed that it was purified to the extent that it was a single band with a molecular weight of about 60 kDa. A molecular weight predicted from the elution condition of the gel filtration chromatography was about 60 kDa, and this enzyme was considered to be present as a monomer.

Example 4: Substrate Characteristics of Aminoacylase Native to *Rhodothermus marinus* (RmELA)

4-1) Acyl Lysine Hydrolysis

To look into the substrate specificity of the acyl lysine hydrolysis of this enzyme, the reactivity of the enzyme as described herein for various kinds of acyl lysines was examined. The results are shown in Table 2 below. The enzyme was evaluated using the purified enzyme acquired in Example 3. Activity measurement was performed with the various kinds of acyl lysines (4 mM) and 100 mM Tris-HCl (pH 7.0) at 37° C., and the activity was calculated by measuring the concentration of lysine produced along with the degradation of the acyl lysines. For the measurement of L-lysine, BF-5 and a lysine electrode (manufactured by Oji Scientific Instruments Co., Ltd.) was used, whereas for the measurement of D-lysine, an amino acid analyzer (manufactured by Hitachi, Ltd.) was used. Here, 1 U was defined as an enzyme amount that releases 1 μmol lysine from each of the acyl lysines (per 1 minute).

TABLE 2

| Hydrolysis activity of RmELA for various kinds of acylamino acids | |
|---|---|
| Acyl lysine | Hydrolysis activity U/mg |
| Nε-Acetyl-L-Lys | 17.5 |
| Nα-Acetyl-L-Lys | 0.0 |
| Nε-Benzoyl-L-Lys | 90.1 |
| Nα-Benzoyl-L-Lys | 0.0 |
| Nε-Acetyl-D-Lys | 0.0 |
| Nε-(αGlu)-L-Lys | 36.8 |
| Nε-(γGlu)-L-Lys | 41.3 |

This enzyme exhibited degradation activity for Nε-acetyl-L-lysine and Nε-benzoyl-L-lysine and did not exhibit hydrolysis activity for Nα-acetyl-L-lysine or Nα-benzoyl-L-lysine and did not exhibit hydrolysis activity for Nε-acetyl-D-lysine. Therefore, it has been demonstrated that this enzyme is an enzyme having high selectivity for the ε-position amino group and L-lysine.

4-2) Acyl Lysine Dehydration Condensation

To look into the substrate specificity of the acyl lysine dehydration condensation of this enzyme, acyl lysine synthesis capability by this enzyme with L-lysine and various kinds of carboxylic acids as substrates was examined. The enzyme was evaluated using the purified enzyme acquired in Example 3. The synthesis reaction was carried out with 45 mM L-lysine hydrochloride, each of the various kinds of carboxylic acids (45 mM), 100 mM Tris-HCl (pH 8.0), 10% (v/v) methanol at 45° C., and the detection of the molecular weight of acyl lysine was revealed by performing mass analysis (DART-MS manufactured by JEOL Ltd.) on the reaction solution.

As a result, it was revealed that this enzyme produces a condensation product of L-lysine and the various kinds of carboxylic acids in the reaction solution. When no enzyme was added, no production of the condensation product was detected.

For an enzyme reaction solution with L-lysine hydrochloride and octanoic acid as substrates and an enzyme reaction solution with L-lysine hydrochloride and dodecanoic acid as substrates, it was revealed by HPLC analysis that Nε-octanoyl-L-lysine and Nε-dodecanoyl-L-lysine are produced, respectively. In these reaction solutions, Nα-octanoyl-L-lysine or Nα-dodecanoyl-L-lysine was not detected, indicating high selectivity for the ε-position amino group. The HPLC analysis was performed with Column YMC-UltraHT Pro C18, 50×2.0 mm ID, S-2 μm, 12 nm (YMC), a mobile layer of 0.3 M $NaH_2PO_4$/MeOH=1/1, and UV 210 nm.

From the above results, it is demonstrated that this enzyme acts on L-lysine and the carboxylic acid to produce Nε-acyl lysine and that the carboxylic acid that can act includes saturated or unsaturated linear aliphatic acids and aromatic carboxylic acids having saturated or unsaturated side chains.

TABLE 3

Examples of carboxylic acids that can undergo dehydration condensation with L-lysine using RmELA

| Caprylic acid CAS: 124-07-2 | 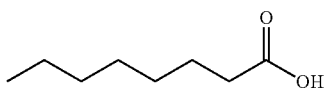 |
|---|---|

TABLE 3-continued

Examples of carboxylic acids that can undergo dehydration condensation with L-lysine using RmELA Lauric acid
CAS: 143-07-7

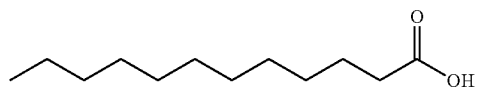

Myristic acid
CAS: 544-63-8

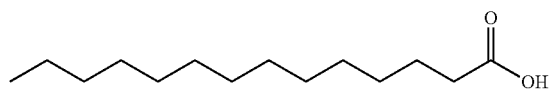 [SMILES: CCCCCCCCCCCCCC(=O)O]

Palmitic acid
CAS: 57-10-3

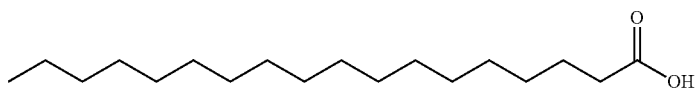 [SMILES: CCCCCCCCCCCCCCCCCC(=O)O]

Linoleic acid
CAS: 60-33-3

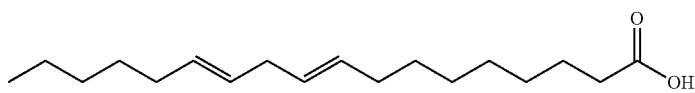 [SMILES: CCCCC/C=C/C/C=C/CCCCCCCC(=O)O]

Oleic acid
CAS: 112-80-1

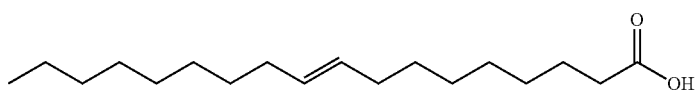 [SMILES: CCCCCCCC/C=C/CCCCCCCC(=O)O]

Benzoic acid
CAS: 65-85-0

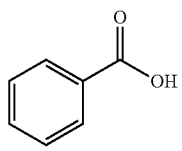

4-Methoxy-3-methylbenzoic acid
CAS: 6880-04-2

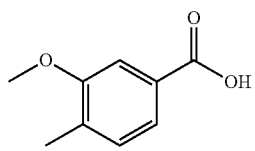

3-Phenylpropionic Acid
CAS: 501-52-0

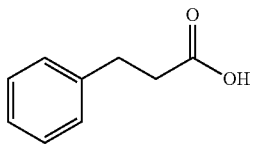 [SMILES: O=C(O)CCc1ccccc1]

Cinnamic acid
CAS: 140-10-3

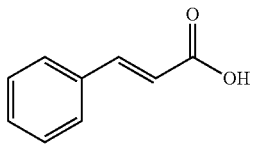 [SMILES: O=C(O)/C=C/c1ccccc1]

4-Methoxycinnamicacid
CAS: 830-09-1

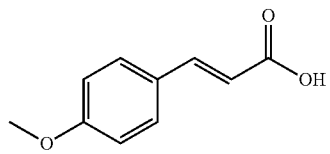

Example 5: Influence of Temperature and pH on Aminoacylase Native to *Rhodothermus marinus* (RmELA)

5-1) Influence on Temperature

Using the purified enzyme acquired by the method described in Example 3, the optimum reaction temperature and temperature stability of the enzyme with Nε-acetyl-L-lysine as a substrate were examined.

Activity at certain temperatures (30° C. to 80° C.) and pH 7.0 (50 mM Tris-HCl buffer) was measured. The results are shown in FIG. 1. The activity was represented as relative activity (%) with the maximum activity value as 100. The optimum reaction temperature of this enzyme was 75° C.

Figure 2:
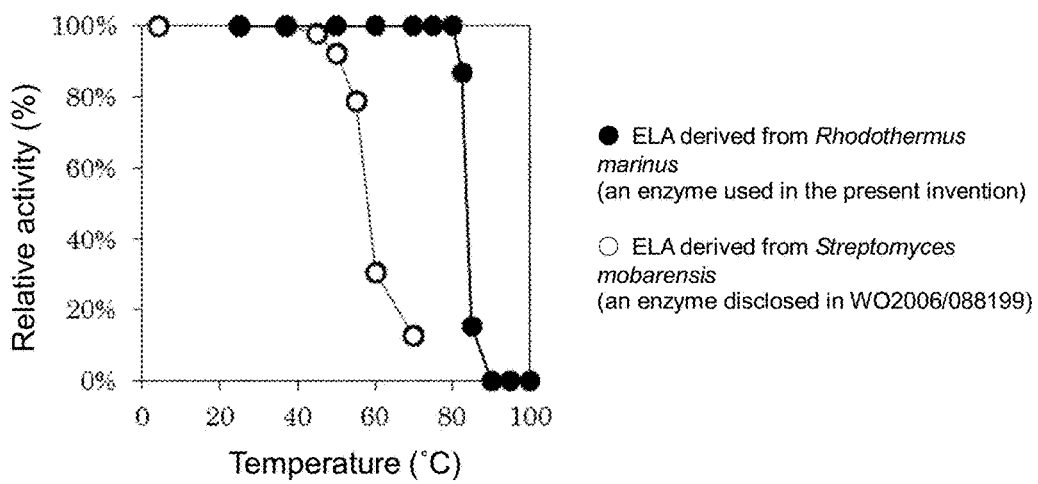
FIG. 2 is a diagram illustrating a temperature stability comparison between ELA native to *Rhodothermus marinus*, as used in the method as described herein, and ELA native to *Streptomyces mobarensis*, as disclosed in WO 2006/088199.

Subsequently, remaining activity after being incubated at certain temperatures (30° C. to 100° C.) for 1 hour was measured. The results are shown in FIG. 2. The activity was represented as relative activity (%) with the activity value before the incubation as 100. When being incubated at each temperature for 1 hour, this enzyme showed no decrease in activity up to 80° C. and was thus stable.

It is known that ELA native to *Streptomyces mobarensis* exhibiting hydrolysis activity for Nε-acetyl-L-lysine decreases in activity when it is incubated at 40° C. or higher for 1 hour; it has been demonstrated that this enzyme is more stable than it.

5-2) Influence on pH

Using the purified enzyme acquired by the method described in Example 3, the optimum pH and pH stability of the enzyme with Nε-acetyl-L-lysine as a substrate were examined.

Figure 3:
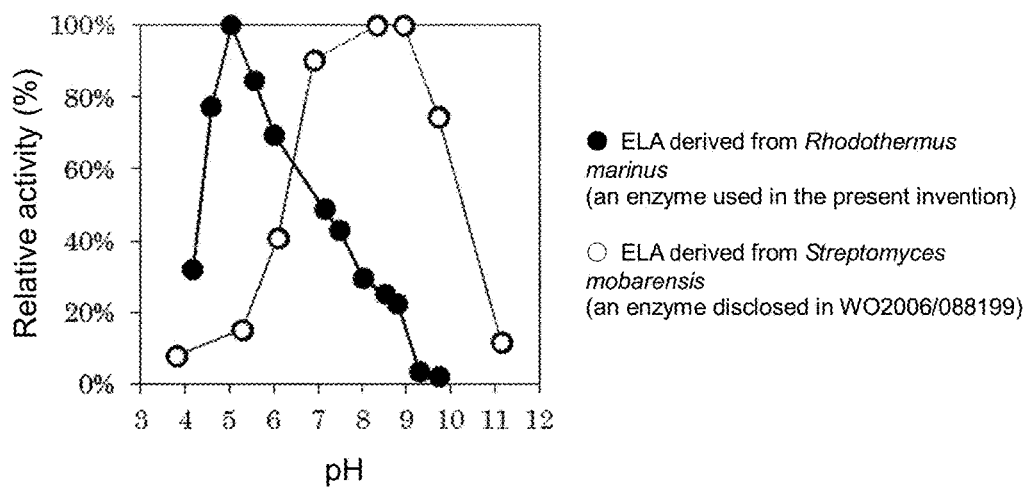
FIG. 3 is a diagram illustrating a pH dependence comparison between ELA native to *Rhodothermus marinus*, as used in the method as described herein, and ELA native to *Streptomyces mobarensis*, as disclosed in WO 2006/088199.

Using various kinds of buffers (pH 4.2 to 6.0: acetate buffers, pH 7.2 to 8.8: Tris-HCl buffers, and pH 9.3 to 9.8: borate buffers) at 37° C., activity at various pH was measured. The results are shown in FIG. 3. The activity was represented as relative activity (%) with the maximum activity value as 100. The optimum pH of this enzyme was pH 5.0.

It has been demonstrated that this enzyme has its optimum pH in a weak acid region (pH 4.5 to 5.5), whereas ELA native to *Streptomyces mobarensis* has its optimum pH in pH 8.0 to pH 9.0 and tends to greatly decrease in activity in a weak acid region of pH 4.0 to 6.0.

Figure 4:
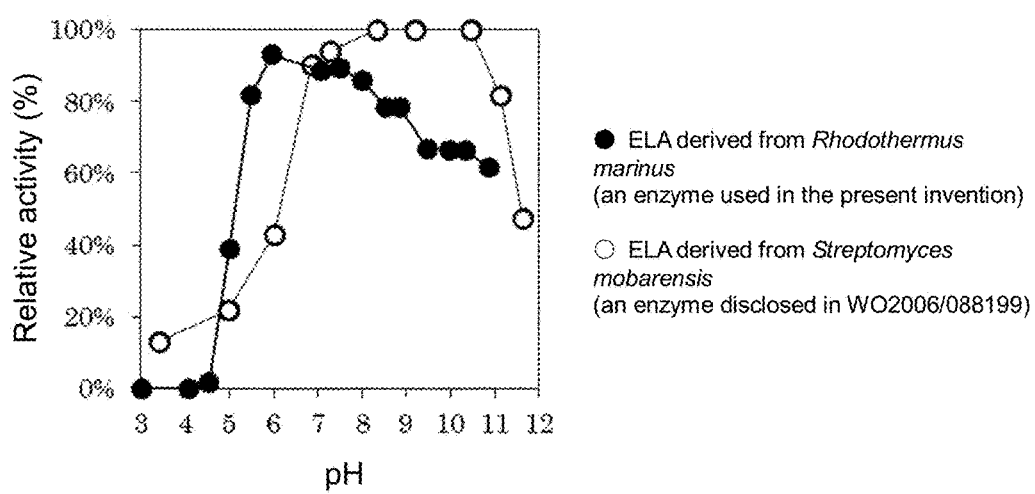
FIG. 4 is a diagram illustrating a pH stability comparison between ELA native to *Rhodothermus marinus*, as used in the method as described herein, and ELA native to *Streptomyces mobarensis*, as disclosed in WO 2006/088199.

Subsequently, remaining activity after being incubated at 37° C. for 1 hour in various kinds of buffers (pH 2.2 to 3.0: phosphate buffers, pH 4.1 to 6.0: acetate buffers, pH 7.1 to 8.9: Tris-HCl buffers, and pH 9.5 to 10.9: borate buffers) was measured. The results are shown in FIG. 4. The activity was represented as relative activity (%) with the activity value before the incubation as 100. This enzyme was stable in the range of pH 6.0 to 8.0 during incubation at 37° C. for 1 hour.

Example 6: Sterilization of RmELA Expression Strain with Enzyme Activity Maintained Whether a *C. glutamicum* expression strain of RmELA could be sterilized with heat while maintaining the enzyme activity was examined. The culture solution acquired by the method described in Example 1, 1-6) in an amount of 150 μl was dispensed to a PCR tube and was subjected to heat treatment at 75° C. for 30 minutes using a block heater to obtain a heat treatment culture solution. The heat treatment culture solution and the heat treatment culture solution serially diluted (with a dilution rate of ×10$^2$) with a physiological saline solution (0.85% of NaCl) were applied to a CM2G agar medium (10 g of a yeast extract, 10 g of polypeptone, 5 g of glucose, 5 g of sodium chloride, 0.2 g of DL-methionine, 15 g of agar, pH 7.2, and filled up to 1 L with water) containing 25 mg/l of kanamycin, and the number of formed colonies was counted to examine the number of living bacteria of the RmELA expression strain. As a result, no colony formation was detected. Therefore, it was revealed that the culture solution was sterilized by the heat treatment at 75° C. for 30 minutes. When a culture solution without the heat treatment was examined by the same method, the number of living bacteria was 7.0×10$^{10}$ cfu/ml.

Subsequently, the culture solution and the heat treatment culture solution explained above were centrifuged individually, the supernatants were collected, and the hydrolysis activity of Nε-acetyl-L-lysine within the supernatants was measured. As a result, comparable enzyme activity values were shown before and after the heat treatment. Therefore, it was revealed that no decrease in enzyme activity by the heat treatment was observed.

From the foregoing results, it was demonstrated that RmELA expression bacteria can be sterilized with heat with the enzyme activity maintained.

Example 7: Storage Stability of Rm-ELA

A culture solution of the *C. glutamicum* expression strain of RmELA acquired by the method described in Example 1, 1-6) was centrifuged to collect the supernatant, which was membrane-sterilized with a 0.45 μm filter to obtain an RmELA enzymatic solution. A WDK010/pPKT-tatABC strain (WO 2010/067871) as a *C. glutamicum* expression strain of ELA native to *Streptomyces mobarensis* (SmELA) was cultured and sterilized by a similar procedure to obtain an SmELA enzymatic solution.

These enzymatic solutions were stored at temperatures of 4° C., 15° C., and 25° C., and the transition of enzyme activity was examined. The results are shown in FIG. 5. The activity was represented as relative activity (%) with the activity value when the storage started as 100. The RmELA enzymatic solution did not decrease in enzyme activity in all the storage temperatures. In contrast, the SmELA enzymatic solution tended to decrease in enzyme activity as the number of days of storage passes; the remaining activity after 37 days decreased to about 60% in the storage at 4° C.

From the foregoing results, it has been demonstrated that the enzyme as described herein (RmELA) can be stored more stably than SmELA.

Example 8: Synthesis of Nε-dodecanoyl-L-lysine by RmELA Enzymatic Solution

Using the RmELA enzymatic solution prepared by the method described in Example 7, the synthesis reaction of Nε-dodecanoyl-L-lysine was carried out. A 200 ml of a reaction solution was prepared so as to give final concentrations of 300 mmol/L dodecanoic acid, 300 mmol/L L-lysine hydrochloride, 0.1 mmol/L ZnSO$_4$, 10% methanol, and 3 U/ml the RmELA enzymatic solution and was stirred at 300 rpm using a 500 ml jar fermenter. The pH was adjusted to be 7.0 using 1 N of NaOH, and the reaction temperature was adjusted to be 55° C.

Figure 6:
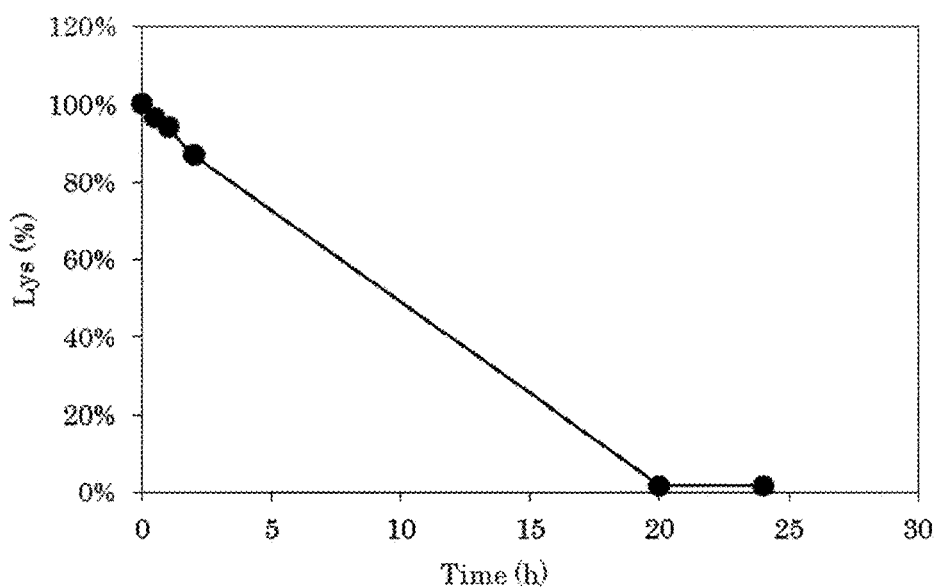
FIG. 6 is a diagram illustrating a temporal change (pH 7.0) of the amount of L-lysine in the synthesis reaction of Nε-dodecanoyl (lauryl)-L-lysine.

During the reaction, the reaction solution was sampled over time, and an L-lysine concentration within the reaction solution was measured, revealing that 98% of the charged L-lysine was consumed after 24 hours (FIG. 6, with the lysine concentration at the start of the reaction as 100%). When the reaction solution after 24 hours was analyzed by HPLC, Nε-dodecanoyl-L-lysine was produced by 98% in terms of yield relative to L-lysine, revealing that the consumed L-lysine was converted into Nε-dodecanoyl-L-lysine. Nα-dodecanoyl-L-lysine was produced by only 0.06% in terms of yield relative to L-lysine.

For the measurement of lysine, BF-5 and a lysine electrode (manufactured by Oji Scientific Instruments Co., Ltd.) were used. The HPLC analysis was performed with Column YMC-UltraHT Pro C18, 50×2.0 mm I.D. (manufactured by YMC Co., Ltd.), a mobile layer of NaH$_2$PO$_4$ (pH 3.0)/MeOH=3/7, and UV 210 nm.

Figure 7:
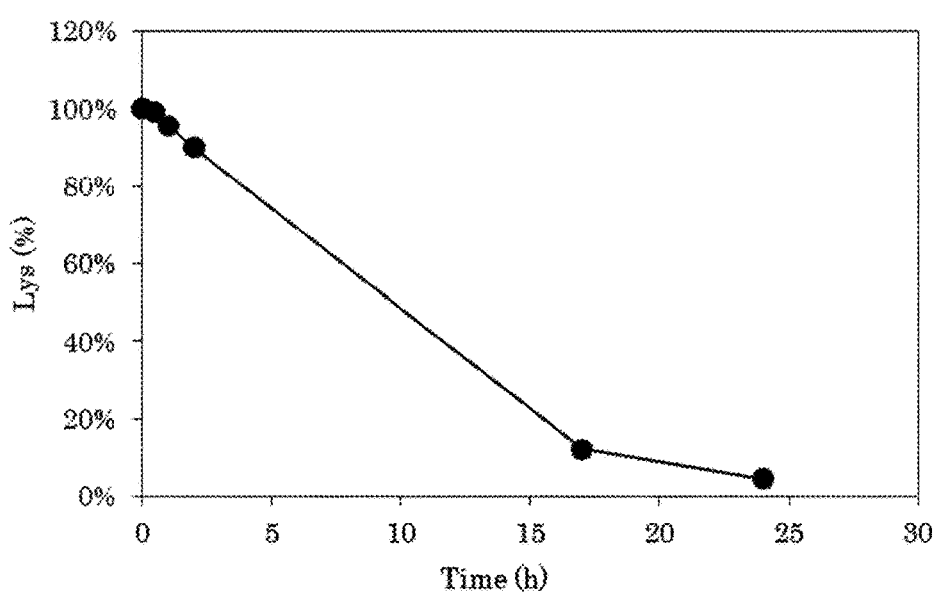
FIG. 7 is a diagram illustrating a temporal change (pH 6.0) of the amount of L-lysine in the synthesis reaction of Nε-dodecanoyl-L-lysine.
Figure 8:
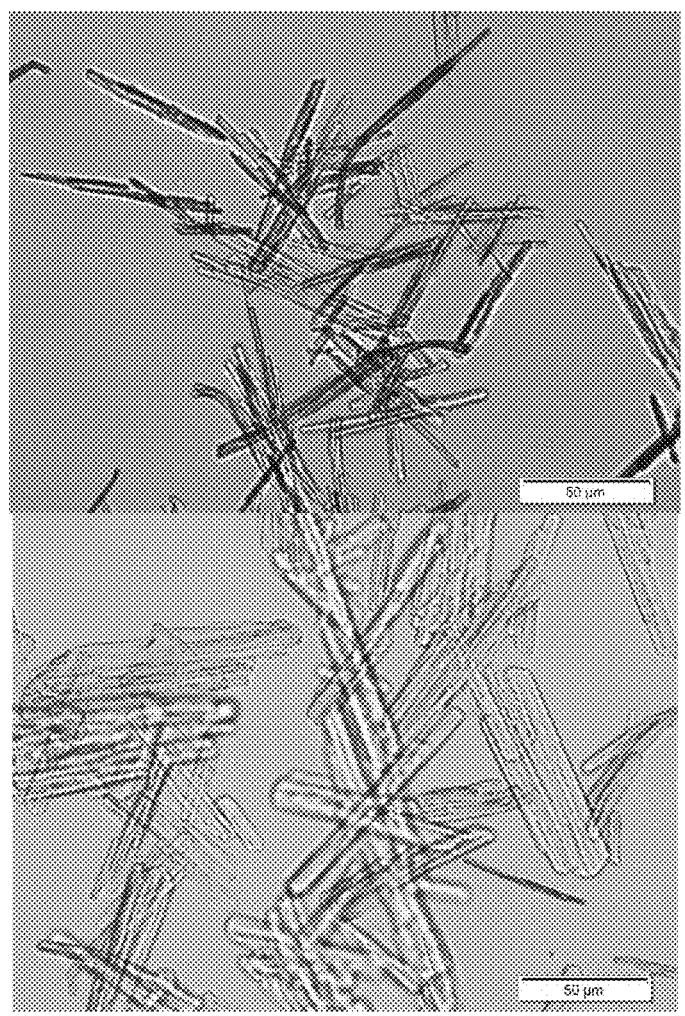
FIG. 8 is diagram illustrating crystals of Nε-dodecanoyl-L-lysine (upper: pH 7.0, lower: pH 6.0).

When the reaction pH was changed from pH 7.0 to pH 6.0, and the synthesis reaction of Nε-dodecanoyl-L-lysine was carried out by a method similar to the above, 96% of the charged L-lysine was consumed after 24 hours (FIG. 7). When the crystal shape of the produced Nε-dodecanoyl-L-lysine was observed with an optical microscope, the short diameter increased three times compared with the crystal produced in the reaction with pH 7.0 (FIG. 8). At pH 7.0, dodecanoic acid in the reaction solution was emulsified to give a high viscosity solution. In contrast, at pH 6.0, the reaction solution separated into the aqueous layer (an L-lysine aqueous solution) and the oil layer (dodecanoic acid) resulting in a low-viscosity solution. It was considered that the difference in the solution property that gave the variation in the crystal formation of Nε-dodecanoyl-L-lysine produced by the enzyme reaction.

It was that ELA native to *Streptomyces mobarensis* (SmELA) has its optimum pH in pH 8.0 to pH 9.0 and greatly decreases in activity in the weak acid region of pH 4.0 to 6.0, and thus the synthesis reaction of Nε-dodecanoyl-L-lysine barely proceeds when the pH is 6.5 or lower (JAOCS, Vol. 82, No. 9, 2005). From the foregoing results, it was demonstrated that the enzyme RmELA as described herein is a novel enzyme that enable synthesis of Nε-dodecanoyl-L-lysine in a weak acid pH region, and that the crystal of Nε-dodecanoyl-L-lysine produced under these conditions tends to have an dincrease short diameter as compared with the crystal produced by the reaction at around pH 7.0, at which dodecanoic acid is emulsified.

Example 9: Synthesis of Nε-octanoyl-L-lysine by RmELA Enzymatic Solution

Using the RmELA enzymatic solution prepared by the method described in Example 7, the synthesis reaction of Nε-octanoyl-L-lysine was carried out. A 100 ml of a reaction solution was prepared so as to give final concentrations of 300 mmol/L octanoic acid, 300 mmol/L L-lysine hydrochloride, 0.1 mmol/L $ZnSO_4$, and 2.1 U/ml the RmELA enzymatic solution and was stirred at 300 rpm using a 200 ml jar fermenter. The pH was adjusted to be 7.0 using 1 N of NaOH, and the reaction temperature was adjusted to be 50° C.

Figure 9:
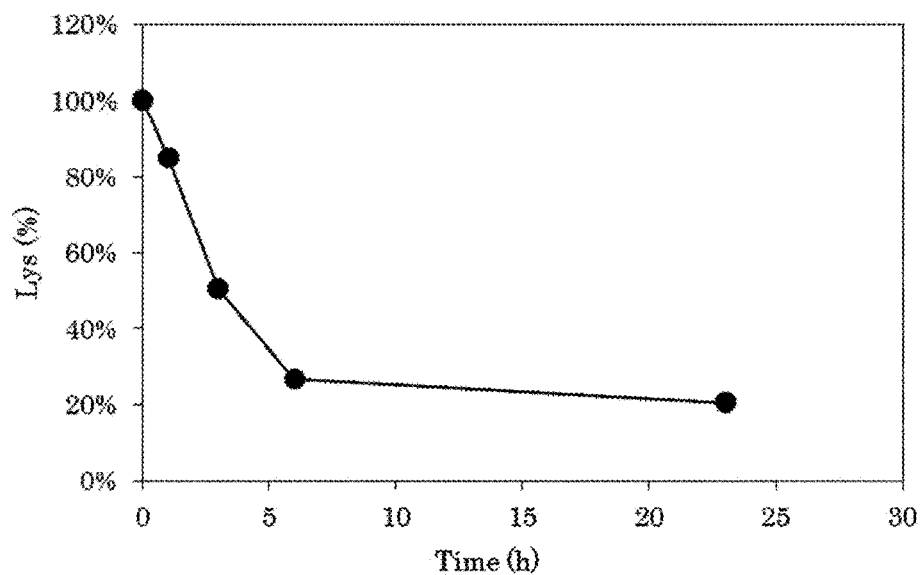
FIG. 9 is a diagram illustrating a temporal change of the amount of L-lysine in the synthesis reaction of Nε-octanoyl (capryloyl)-L-lysine.

During the reaction, the reaction solution was sampled over time, and an L-lysine concentration within the reaction solution was measured. As a result, it was revealed that 80% of the charged L-lysine was consumed after 23 hours (FIG. 9, with the lysine concentration at the start of the reaction as 100%). When the reaction solution after 23 hours was analyzed by HPLC, Nε-octanoyl-L-lysine was produced by 80% in terms of yield relative to L-lysine. Threfore, it was revealed that the consumed L-lysine was converted into Nε-octanoyl-L-lysine. No peak of Nα-octanoyl-L-lysine was detected.

The HPLC analysis was performed under an elution condition of eluent: MeOH/phosphate buffer 50/50 (15 minutes)→gradient (15 minutes)→90/10→gradient (3 minutes)→50/50 (12 minutes) (phosphate buffer=$H_3PO_4$ was added to 0.1 mol/L-$NaH_2PO_4$ aq. to adjust pH to 2.5) using Column YMC-Pack ODS-A 150×6.0 mm I.D., S-5 µm, 12 nm (manufactured by YMC Co., Ltd., product No. AA12S05-1506WT).

The substrate (octanoic acid and L-lysine hydrochloride) final concentration in the reaction condition was changed to (1) 500 mmol/L, (2) 750 mmol/L, and (3) 1,000 mmol/L to carry out the synthesis reaction of Nε-octanoyl-L-lysine.

Figure 10:
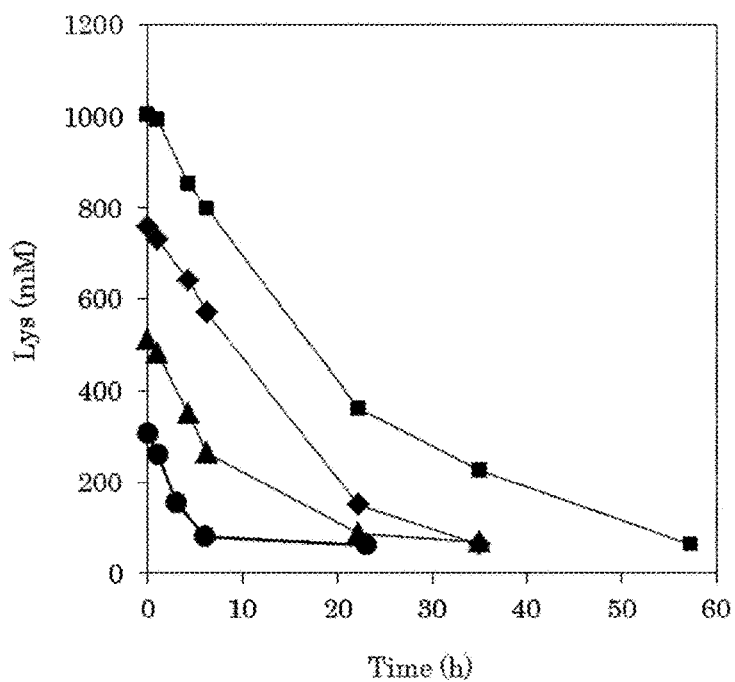
FIG. 10 is a diagram illustrating a temporal change (RmELA) of the amount of L-lysine in the synthesis reaction of Nε-octanoyl-L-lysine.

During the reaction, the reaction solution was sampled over time, and an L-lysine concentration in the reaction solution was measured. As a result, it was revealed that L-lysine decreased over the reaction time under various conditions, and the synthesis reaction of Nε-octanoyl-L-lysine proceeded (FIG. 10). Respective consumption rates relative to the charged L-lysine and reaction times were (1) 87% after 35 hours, (2) 92% after 35 hours, and (3) 94% after 57 hours.

Figure 11:
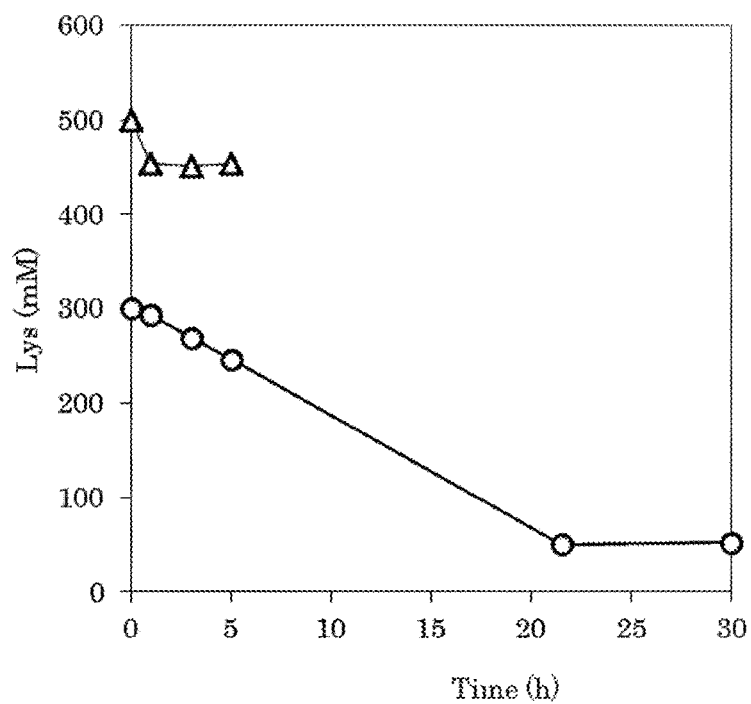
FIG. 11 is a diagram illustrating a temporal change (SmELA) of the amount of L-lysine in the synthesis reaction of Nε-octanoyl-L-lysine.

The synthesis reaction of Nε-octanoyl-L-lysine was carried out similarly using ELA native to *Streptomyces mobarensis* (SmELA), revealing that when the substrate (octanoic acid and L-lysine hydrochloride) final concentration is 300 mmol/L, the amount of L-lysine decreased over the reaction time and that the synthesis reaction of Nε-octanoyl-L-lysine proceeded (FIG. 11). In contrast, it was revealed that when the substrate is at final concentration of 500 mmol/L, there is no change in the amount of L-lysine in the reaction solution and that no reaction proceeded (FIG. 11). It was predicted that enzyme activity was inactivated or the reaction was inhibited by the increasing substrate concentration.

From the foregoing result, it has been demonstrated that the enzyme RmELA as described herein allows the Nε-octanoyl-L-lysine synthesis reaction to proceed even at substrate (octanoic acid and the L-lysine hydrochloride) concentrations that are know to cause inhibition of the reaction when using the known enzyme SmELA.

The conditions other than the substrate final concentration in the synthesis reaction of Nε-octanoyl-L-lysine by SmELA were performed as follows. A 100 ml of a reaction solution was prepared so as to give final concentrations of 0.1 mmol/L $ZnSO_4$ and 5.7 U/ml the SmELA enzymatic solution and was stirred at 300 rpm using a 200 ml jar fermenter. The pH was adjusted to be 8.0 using 1 N NaOH, and the reaction temperature was adjusted to be 30° C.

The activity value of the SmELA enzymatic solution was calculated from the concentration of lysine produced along with the hydrolysis of Nε-acetyl-L-lysine with 40 mM Nε-acetyl-L-lysine and 50 mM Tris-HCl (pH 8.0) at 37° C. Here, 1 U was defined as an enzyme amount that isolates 1 µmol of lysine from Nε-acetyl-L-lysine (per 1 minute).

INDUSTRIAL APPLICABILITY

The present invention is useful for the production of Nε-acyl-L-lysine.

The invention claimed is:

1. A method for producing Nε-acyl-L-lysine comprising reacting a carboxylic acid or a salt thereof and L-lysine or a salt thereof in the presence of a protein to produce Nε-acyl-L-lysine and collecting said Nε-acyl-L-lysine, wherein the protein is selected from the group consisting of:
   (A) a protein comprising the amino acid sequence of SEQ ID NO: 1;
   (B) a protein comprising the amino acid sequence of SEQ ID NO: 1, but in which no more than one to 50 amino acid residues are inserted, added, deleted, or substituted and wherein said protein has Nε-acyl-L-lysine-specific aminoacylase activity; and
   (C) a protein comprising an amino acid sequence having 90% or higher sequence identity with the amino acid sequence of SEQ ID NO: 1 and wherein said protein has Nε-acyl-L-lysine-specific aminoacylase activity.

2. The method according to claim 1, wherein the protein is native to a bacterium belonging to the genus *Rhodothermus*.

3. The method according to claim 1, wherein the protein is purified.

4. The method according to claim 1, wherein said reacting is carried out using i) a microorganism producing the protein or ii) a treatment solution comprising a microorganism producing the protein.

5. The method according to claim 4, wherein the microorganism is a bacterium belonging to the genus *Corynebacterium*.

6. The method according to claim 5, wherein the microorganism is *Corynebacterium glutamicum*.

7. The method according to claim 1, wherein the carboxylic acid has five or more carbon atoms.

8. The method according to claim 1, wherein the carboxylic acid is selected from the group consisting of octanoic acid, dodecanoic acid, tetradecanoic acid, hexadecanoic acid, linoleic acid, oleic acid, benzoic acid, methoxymethyl benzoic acid, phenylpropionic acid, cinnamoyl acid, and methoxycinnamoyl acid.

9. The method according to claim 1, wherein the carboxylic acid is octanoic acid or dodecanoic acid, and Nε-acyl-L-lysine is Nε-octanoyl-L-lysine or Nε-dodecanoyl-L-lysine.

10. The method according to claim 1, wherein said reacting is carried out in an aqueous solvent.

11. The method according to claim 4, wherein the treatment solution is a microbicidal treatment solution.

12. The method according to claim 1, wherein said reacting is carried out at 40° C. or higher.

13. The method according to claim 1, wherein the carboxylic acid or a salt thereof is non-emulsified.

14. The method according to claim 1, wherein said reacting is carried out in a solution comprising the carboxylic acid or a salt thereof, or L-lysine or a salt thereof in a concentration of 500 mmol/L or higher.

15. A method for producing Nε-acyl-L-lysine comprising reacting a carboxylic acid or a salt thereof and L-lysine or a salt thereof in the presence of a protein to produce Nε-acyl-L-lysine and collecting said Nε-acyl-L-lysine, wherein the protein is selected from the group consisting of:
  (A) a protein comprising the amino acid sequence of SEQ ID NO: 1;
  (B) a protein comprising the amino acid sequence of SEQ ID NO: 1, but in which no more than one to 30 amino acid residues are inserted, added, deleted, or substituted and wherein said protein has Nε-acyl-Llysine-specific aminoacylase activity; and
  (C) a protein comprising an amino acid sequence having 95% or higher sequence identity with the amino acid sequence of SEQ ID NO: 1 and wherein said protein has Nε-acyl-L-lysine-specific aminoacylase activity.

* * * * *

SEQUENCE LISTING

```
<160> NUMBER OF SEQ ID NOS: 13

<210> SEQ ID NO 1
<211> LENGTH: 553
<212> TYPE: PRT
<213> ORGANISM: Rhodothermus marinus

<400> SEQUENCE: 1

Met Leu Leu Leu Pro Met Gln Ala Arg Gly Gln Ala Asp Tyr Val Leu
1               5                   10                  15

Val Asn Gly Arg Leu Tyr Thr Val Asp Pro Ala Gln Pro Val Ala Glu
            20                  25                  30
```

```
Ala Met Ala Val Arg Gly Asp Arg Ile Leu Met Val Gly Thr Thr Ala
         35                  40                  45
Gln Leu Thr Ala Ala Tyr Pro Asp Ala Pro His Ile Asp Leu Gln Gly
 50                  55                  60
Arg Ala Val Pro Gly Phe Ile Asp Ala His Ala His Leu Met Gly
 65                  70                  75                  80
Leu Gly Leu Ser Arg Leu Arg Ala Asp Leu Thr Gly Thr Arg Ser Val
                 85                  90                  95
Glu Glu Ile Leu Glu Arg Leu Arg Glu Phe Ala Arg Gln Leu Pro Glu
                100                 105                 110
Gly Ala Trp Leu Leu Gly Arg Gly Trp Asp Gln Asn Asp Trp Pro Val
            115                 120                 125
Lys Glu Phe Pro Thr Arg Gln Met Leu Asp Glu Ile Phe Pro Glu Arg
130                 135                 140
Pro Val Trp Leu Val Arg Ile Asp Gly His Ala Ala Trp Ala Asn Thr
145                 150                 155                 160
Ala Ala Ile Arg Arg Ala Asn Pro Ala Leu Leu Thr Glu Gln Ile Pro
                165                 170                 175
Asp Pro Glu Gly Gly His Ile Val Arg Asp Ala Glu Gly Arg Leu Thr
                180                 185                 190
Gly Val Phe Ile Asp Glu Ala Met Asp Leu Ile Ala Arg His Ile Pro
            195                 200                 205
Pro Pro Ser Glu Ala Glu Leu Glu Glu Ala Leu Arg Arg Ala Val Ala
        210                 215                 220
Glu Ala Asn Arg Phe Gly Leu Thr Gly Val His Asp Ala Gly Ala Ser
225                 230                 235                 240
Leu Lys Thr Ile Gln Gly Tyr Arg Arg Ala Val Asp Asp Gly Thr Leu
                245                 250                 255
Thr Leu Arg Leu Tyr Val Met Val Asp Gly Leu Gly Glu Ala Phe Asp
                260                 265                 270
Tyr Phe Cys Glu His Gly Pro Leu Leu Asp Tyr Gly Gly Arg Leu Thr
            275                 280                 285
Val Arg Ser Val Lys Phe Tyr Ile Asp Gly Ala Leu Gly Ser Arg Gly
        290                 295                 300
Ala Ala Leu Leu Ala Asp Tyr Ser Asp Asp Pro Gly Asn Arg Gly Leu
305                 310                 315                 320
Leu Arg His Glu Pro Glu Val Phe Ala Asp Met Val Gln Arg Ala Met
                325                 330                 335
Lys Cys Gly Phe Gln Val Asn Thr His Ala Ile Gly Asp Arg Gly Val
            340                 345                 350
Arg Val Val Leu Asp Ala Tyr Glu Lys Ala Leu Arg Thr Leu Gly Arg
        355                 360                 365
Thr Val Gly Arg His Arg Val Glu His Ala Gln Val Val Ala Pro Glu
        370                 375                 380
Asp Phe Ala Arg Phe Ala Glu Leu Asp Leu Ile Ala Ser Met Gln Pro
385                 390                 395                 400
Thr His Ala Thr Ser Asp Met Tyr Trp Ala Glu Asp Arg Leu Gly Pro
                405                 410                 415
Glu Arg Val Arg Gly Ala Tyr Ala Trp Arg Thr Phe Leu Glu His Gly
            420                 425                 430
Val Arg Leu Ala Phe Gly Ser Asp Phe Pro Val Glu Leu Ala Asn Pro
        435                 440                 445
```

Leu Leu Gly Phe Tyr Ala Ala Ile Thr Arg Gln Asp Ala Glu Gly Trp
            450                 455                 460

Pro Glu Gly Gly Trp Tyr Pro Glu Gln Arg Leu Thr Arg Glu Ala
465                 470                 475                 480

Leu Arg Ala Phe Thr Leu Asp Ala Ala Tyr Ala Ala Phe Gln Glu His
                485                 490                 495

Glu Leu Gly Ser Leu Thr Pro Gly Lys Tyr Ala Asp Phe Val Val Leu
            500                 505                 510

Ser His Asp Ile Met Thr Val Pro Glu Gln Ile Leu Gln Thr Arg
            515                 520                 525

Val Leu Ala Thr Phe Phe Gly Gly Arg Cys Val Tyr His Asp Pro Glu
530                 535                 540

Ala Ala Gly Leu Cys Pro Ala Ser Pro
545                 550

<210> SEQ ID NO 2
<211> LENGTH: 1659
<212> TYPE: DNA
<213> ORGANISM: Rhodothermus marinus

<400> SEQUENCE: 2

```
cggcgaagcc gggcacaggc cggcggcttc agggtcgtgg tagacgcacc gccccccgaa      60
aaaggtggcc agcacccggg tttgcaggat ttgctccggc ggcacggtca tgatgtcgtg     120
tgaaagcacg acgaaatcgg catacttgcc gggcgtcagc gagcccagct cgtgctcctg     180
aaaggcggca taggcggcgt cgagcgtaaa ggcgcggagc gcttcctcgc gggtgagtcg     240
ctgctcggga taccagccac cttccggcca gccctcggcg tcctgccgcg tgatcgccgc     300
atagaagccc agcagcggat ggccaactcg acggggaaaa tcagagccga aagccagccg     360
cacgccgtgc tccaggaacg tgcgccaggc gtaggcgccg cgcacgcgct cgggcccccag     420
tcggtcttcg gcccagtaca tgtcgctggt ggcgtgcgtc ggttgcatcg acgcgatcag     480
gtccagctcg gcaaaacgcg caaaatcctc cggcgccacc acctgggcat gctccacgcg     540
gtgccgcccc accgtgcgtc ccagcgtgcg cagcgctttc tcgtaggcat ccagcaccac     600
gcgcacgccc cggtcgccga tggcgtgcgt gttgacctgg aagccgcact tcatcgctcg     660
ctgcaccatg tcagcaaaca cctcgggctc gtggcgcagc aatccacggt tacccggatc     720
gtcgctgtaa tccgccagca gtgcagcccc ccgactgccc agggcccgt cgatgtagaa     780
cttgacggag cgcacggtca gccgcccgcc gtagtccagc aggggcccgt gctcacagaa     840
gtagtcgaac gcctccccga daccgtccac catcacgtaa agccgaagcg tcagcgtccc     900
gtcgtccacg gctcgccgat agccctggat ggtcttcagg ctggccccgg cgtcgtgcac     960
gcccgtcagt ccgaagcggt tggcctcggc cacggcccgg cgcaaggctt cttccagctc    1020
ggcctccgaa ggcggcggga tgtggcgggc gatcaggtcc atcgcctcgt cgatgaacac    1080
gcccgtgaga cgcccttcgg catcgcgcac aatgtgtccg cctcgggat cgggaatctg    1140
ctcggtgagc agtgccggat tggcccgtcg gatggcggcc gtgttggccc aggcggcgtg    1200
tccgtcgatg cgcaccagcc agaccggccg ctccggaaag atctcgtcta gcatctgtcg    1260
cgtggggaat tccttcacgg gccagtcgtt ctggtcccag ccccggccca gcagccaggc    1320
accttcggga agctgacggg cgaactcccg caaacgctcc aggatttcct cgacggagcg    1380
cgtgccggtc agatcggccc gcaggcgact caggcccagc ccatcaggt gggcatgtgc    1440
gtcgatgaat cccggcacga cggcgcggcc ctgcaggtcg atgtgcggcg cgtcgggata    1500
```

```
ggcggccgtc agttgcgcgg tagtacctac catcaggatg cgatcgcccc gcacggccat    1560
ggcctcggcc accggctgtg cgggatcgac cgtgtagagc cgtccgttga ccagcacgta    1620
gtcggcctgt ccgcgcgcct gcatgggaag tagcagcat                            1659

<210> SEQ ID NO 3
<211> LENGTH: 2367
<212> TYPE: DNA
<213> ORGANISM: Artificial Sequence
<220> FEATURE:
<223> OTHER INFORMATION: Nucleotide sequence encoding amino acid
      sequence of aminoacylase from Rhodothermus marinus, which has
      modified codons

<400> SEQUENCE: 3
ggtacccaaa ttcctgtgaa gtagctgatt tagtactttt cggaggtgtc tattcttacc      60
aaatcgtcaa gttgtgggta gagtcacctg aatattaatt gcaccgcacg ggtgatatat    120
gcttatttgc tcaagtagtt cgaggttaag tgtattttag gtgaacaaat ttcagcttcg    180
ggtagaagac tttcgatgcg cttcagagct tctattggga aatctgacac cacttgatta    240
aatagcctac ccccgaattg ggggattggt cattttttgc tgtgaaggta gttttgatgc    300
atatgacctg cgtttataaa gaaatgtaaa cgtgatcaga tcgatataaa agaaacagtt    360
tgtactcagg tttgaagcat tttctccgat tcgcctggca aaaatctcaa ttgtcgctta    420 cagttttttct caacgacagg ctgctaagct gctagtrcgg tggcctagtg agtggcgttt    480
acttggataa agtaatccc atgtcgtgat cagccatttt gggttgtttc catagcaatc     540
caaaggtttc gtctttcgat acctattcaa ggagccttcg cctctatgaa caataacgat    600
ctctttcagg catcacgtcg gcgttttctg gcacaactcg gcggcttaac cgtcgccggg    660
atgctggggc cgtcattgtt aacgccgcga cgtgcgactg cgctcctcct ccctatgcag    720
gcacgcggtc aggcagatta cgtcctcgtc aacggtcgtc tctacaccgt ggatccggca    780
cagccagttg cagaagctat ggccgtgcgc ggtgatcgta tcttgatggt cggcaccacc    840
gctcagctga ccgcagctta ccctgatgca cctcacatcg atctgcaggg tcgtgcagtg    900
gtccctggtt tcattgatgc gcacgcacac ctgatgggtc tgggtctctc ccgcctccgt    960
gcagacctta ccggcacccg ctctgtcgaa gagatcttgg aacgcctgcg tgagttcgca   1020
cgccagctgc cagaaggtgc cttggctgct cggtcgtggtt gggatcagaa cgactggcct   1080
gttaaggagt tcccgacccg ccagatgttg gatgaaatct cccagagcg ccctgtctgg   1140 ctggttcgta ttgacggtca cgcagcatgg gcaaacaccg cagctatccg ccgtgcaaac   1200
ccagctcttt tgaccgaaca gatcccggat ccagagggcg gtcacattgt tcgcgacgct   1260
gaaggtcgtc tcaccggcgt gttcattgat gaggccatgg accttatcgc gcgccacatc   1320
ccaccaccat ccgaagcaga gttggaagag gctctgcgcc gtgctgttgc agaggcaaac   1380
cgtttcggcc tcaccggtgt gcacgatgca ggtgcttctc ttaagaccat ccagggctac   1440
cgccgtgcag tcgatgacgg cacccttacc ttgcgcctgt acgttatggt ggatggcctg   1500
ggtgaagcat tcgactactt ctgcgagcac ggcccactgc tcgactacgg cggtcgcttg   1560
accgtgcgtt ccgtcaaatt ctacatcgat ggcgctcttg gttcccgcgg tgcagcactt   1620
ttggcagact actctgatga ccctggtaac cgcggcctgc tccgtcacga accagaagtg   1680
ttcgccgaca tggtgcagcg cgcgatgaag tgtggcttcc aggtcaacac ccacgctatc   1740
ggtgatcgcg gcgttcgtgt tgtgctcgac gcctacgaaa aagcactccg taccccttggt   1800 cgtaccgtcg gtcgtcaccg tgttgagcac gcacaggtcg ttgctccaga agatttcgcc   1860
```

```
cgcttcgcgg agctcgacct tattgcctcc atgcagccaa cccacgcgac ctctgatatg    1920
tactgggcag aagaccgtct gggtcctgag cgtgtgcgtg gtgcctacgc gtggcgcacc    1980
ttcctcgaac acggtgtgcg tcttgcattc ggctccgatt tcccagtcga gctcgctaac    2040
cctcttttgg gcttctacgc agctatcacc cgccaggacg cagaaggttg gccggaaggc    2100
ggctggtatc cagaacagcg cctgacccgt gaagaggcac tccgtgcttt caccccttgat   2160 gccgcgtacg cagcttttcca ggaacacgag ttgggttccc tgaccccggg caaatacgct    2220
gatttcgtgg tcctctctca cgacatcatg accgttccac ctgaacagat tttgcagacc    2280
cgcgtgctgg ctaccttctt cggcggtcgt tgcgtctacc acgacccaga ggcagcaggt    2340
ctgtgtccgg cctccccata agggccc                                         2367
```

```
<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
cgagccacca ggcaggcggg aaaatcg                                          27

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5 cgatttccc gcctgcctgg tggctcg                                           27

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cccgcttgat cattcctta agg                                               23

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
aatgggccct ttggtacccc taaataatat cggtcc                                36

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
cgtgctctag gggaaccgtg cgttccc                                          27
```

```
<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
gggaacgcac ggttccccta gagcacg                                           27

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgacgctgaa gttgtagaga tcatccg                                           27

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
cggatgatct ctacaacttc agcgtcg                                           27

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
aaacatatgc tcctcctccc tatgcaggca                                        30

<210> SEQ ID NO 13
<211> LENGTH: 37
<212> TYPE: DNA
<213> ORGANISM: Artificial Sequence
<220> FEATURE:
<223> OTHER INFORMATION: Primer

<400> SEQUENCE: 13
aaaactcgag tggggaggcc ggacacagac ctgctgc                                37
```